United States Patent [19]
Crooks et al.

[11] Patent Number: 5,830,904
[45] Date of Patent: Nov. 3, 1998

[54] LOBELINE COMPOUNDS AS A TREATMENT FOR PSYCHOSTIMULANT ABUSE AND WITHDRAWAL, AND FOR EATING DISORDERS

[75] Inventors: Peter A. Crooks; Linda P. Dwoskin, both of Lexington, Ky.

[73] Assignee: University of Kentucky Research Foundation, Lexington, Ky.

[21] Appl. No.: 795,852

[22] Filed: Feb. 5, 1997

[51] Int. Cl.[6] ............................................... A61K 31/445
[52] U.S. Cl. ............................................................ 514/317
[58] Field of Search ............................................ 514/317

[56] References Cited

U.S. PATENT DOCUMENTS

| | | | |
|---|---|---|---|
| 3,901,248 | 8/1975 | Lictneckert et al. | 131/2 |
| 4,971,079 | 11/1990 | Talapin et al. | 131/359 |
| 5,272,144 | 12/1993 | Melloni et al. | 514/227.5 |
| 5,403,595 | 4/1995 | Kitchell et al. | 424/501 |
| 5,414,005 | 5/1995 | Schneider et al. | 514/343 |
| 5,468,755 | 11/1995 | Cincotta et al. | 514/288 |
| 5,486,362 | 1/1996 | Kitchell et al. | 424/426 |
| 5,536,503 | 7/1996 | Kitchell et al. | 424/449 |
| 5,552,429 | 9/1996 | Wong et al. | 514/415 |
| 5,576,321 | 11/1996 | Krushinski, Jr. et al. | 514/255 |

FOREIGN PATENT DOCUMENTS

WO92/19241  11/1992  WIPO .

OTHER PUBLICATIONS

Olin, B.R. et al., "Smoking Deterrents," *In Drug Facts and Comparisons*. 1995 edition, ed. by B.R. Olin et al., pp. 3087–3095, St. Louis, MO: J.B. Lippincott Co., 1995.

Sloan, J.W. et al., "The comparative binding characteristics of nicotinic ligands and their phamracology," *Pharmacol. Biochem. Behav.*, 30:255–267 (1988).

Hamann, S.R. et al., "Hyperalgesic and analgesic actions of morphine, U50–448, naltrexone, and (–)lobeline in the rat brainstem," *Pharmacol. Biochem. Behav.*, 47:197–201 (1994).

Brioni, J.D. et la., "Nicotinic receptor agonist exhibit anxiolytic–like effects on the elevated plus–maze test," *Eur. J. Pharmacol.*, 238:1–8 (1993).

Decker, M.W. et al., "Effects of lobeline, a nicotinic receptor agonist, on learning and memory," *Pharmacol. Biochem. Behav.*, 45:571–576 (1993).

Nunn–Thompson et al., "Pharmacotherapy for smoking cessation," *Clin. Pharmacy.*, 8:710–720 (1989).

Prignot, J., "Pharmacological approach to smoking cessation," *Eur. Respir. J.*, 2:550–560 (1989).

Kalyuzhnyy, V.V., "The treatment of nicotinism with the aid of lobeline and its influence on vegetative and vascular reactions," *J. Neural. Psychiat.*, 68:1864–1870 (1968).

Stolerman, I.P. et al., "Dissociation between the locomotor stimulant and depressant effects of nicotinic agonists in rats," *Psychopharmacol.*, 117:430–437 (1995).

Fudala, P.J. et al., "Further studies on nicotine–induced conditioned place preference in the rat," *Pharmacol. Biochem. Behav.*, 25:1041–1049 (1986).

Geller, I. et al., "Effects of nicotine monomethiodide, lobeline, chlordiazepoxide, memprobamate and caffeine on a discrimination task in laboratory rats," *Psychopharmacol. (Berl.)*, 20:355–365 (1971).

Schechter, M.D. et al., "Nicotine as a discriminative cue in rats: inability of related drugs to produce a nicotine–like cuing effect," *Psychopharmacol. (Berl.)*, 27:379–387 (1972).

Reavill, C. et al., "Behavioral and pharmacokinetics studies on nicotine, cytosine and lobeline," *Neuropharmacol.*, 29(7):619–624 (1990).

Romano, C. et al., "Stereospecific nicotine receptors on rat brain membranes," *Science*, 210:647–650 (1980).

Decker, M.W. et al., "Diversity of neuronal nicotinic actylcholine receptors: lessons from behavior and implications for CNS therapeutics," *Life Sci.*, 56:545–570 (1995).

Yamada, S. et al., "Brain nicotinic acetylcholine receptors biochemical characterization by neosurugatoxin," *Mol. Pharmacol.*, 28:120–127 (1985).

Lippiello, P.M. et al., "The binding of L–[$^3$H]nicotine to a single class of high affinity sites in rat brain membrane," *Mol. Pharmacol.*, 29:448–454 (1986).

S. Martin et al., *"Opioid and nicotinic Med Llary Hyperalgesic Influences in the Decerebrated Rat"Pharmacol Biohcem and Behav.*29 725–731 1988.

Broussolle, E.P. et al.,"In vivo binding of $^3$H–nicotine in the mouse brain," *Life Sci.*, 44:1123–1132 (1989).

Bhat, R.V. et al., "Regulation of brain nicotinic receptors by chronic agonist infusion,"*J. Neurochem.*, 56(6):1932–1939 (1991).

Sakurai, Y. et al., "Enhancement of [$^3$H]dopamine release and its [$^3$H]metabolites in rat striatum by nicotinic drugs," *Brain Res.*, 242:99–106 (1982).

Takano, Y. et al., "Presynaptic modulation of the release of dopamine from striatal synaptosomes: difference in the effects of high K$^+$ stimulation, methamphetamine and nicotinic drugs," *Brain Res.*, 279:330–334 (1983).

Grady, S. et al., "Characterization of nicotine receptor–mediated $^3$H–dopamine release from synaptosomes prepared from mouse striatum," *J. Neurochem.*, 59:848–856 (1992).

*Primary Examiner*—Phyllis G. Spivack
*Attorney, Agent, or Firm*—McDermott, Will & Emery

[57] ABSTRACT

Methods are disclosed that suggest the use of lobeline and analogs thereof in treating individuals for drug dependence and withdrawal and for eating disorders.

9 Claims, 6 Drawing Sheets

LOBELINE COMPOUNDS AS A TREATMENT FOR PSYCHOSTIMULANT ABUSE AND WITHDRAWAL, AND FOR EATING DISORDERS

FIELD OF THE INVENTION

The present invention relates to the use of lobeline and analogs thereof in the treatment of drugs of abuse and withdrawal therefrom. The invention also relates to the treatment of eating disorders, such as obesity.

BACKGROUND OF THE INVENTION

Lobeline (α-lobeline) is a lipophilic, non-pyridino, alkaloidal constituent of Indian tobacco (*Lobelia inflata*). As shown by the following formulas, no obvious structural resemblance to S(−)nicotine is apparent:

S(−)Nicotine 2S,6R,8S(−)Lobeline

Structure-function relationships between nicotine and lobeline do not suggest a common pharmacophore (Barlow and Johnson, 1989). Nonetheless, lobeline has been reported to have many nicotine-like effects including tachycardia and hypertension (Olin et al., 1995), bradycardia and hypotension in urethane and pentobarbital anesthetized rats (Sloan et al., 1988), hyperalgesia (Hamann and Martin, 1994), anxiolytic activity (Brioni et al., 1993), and improvement of learning and memory (Decker et al., 1993). Moreover, lobeline has been used as a substitution therapy for tobacco smoking cessation (Nunn-Thompson and Simon, 1989; Prignot, 1989; Olin et al., 1995); however, its effectiveness is controversial as reflected by both positive (Dorsey, 1936; Kalyuzhnyy, 1968) and negative reports (Wright and Littauer, 1937; Nunn-Thompson and Simon, 1989). Furthermore, only short-term usage of lobeline as a smoking deterrent has been recommended due to its acute toxicity (nausea, severe heartburn and dizziness) and the lack of information concerning its long-term usage (Wright and Littauer, 1937; Olin et al., 1995).

In behavioral studies, nicotine has been shown to increase locomotor activity (Clarke and Kumar, 1983a, 1983b; Clarke, 1990; Fung and Lau, 1988), and to produce conditioned place preference (Shoaib et al., 1984); Fudala et al., 1985) in rats. However, the results of the latter studies are controversial (Clarke and Fibiger, 1987). In contrast, lobeline does not increase locomotor activity (Stolerman et al., 1995) or produce conditioned place preference (Fudala and Iwamoto, 1986). Although initially lobeline was shown to generalize to nicotine in discrimination studies (Geller et al., 1971), most subsequent studies have failed to reproduce this original finding (Schechter and Rosecrans, 1972; Reavill et al., 1990; Romano and Goldstein, 1980).

Nicotine has been reported to be avidly self-administered by rats (Corrigal et al. 1992, 1994; Donny et al., 1996); however, the ability of lobeline to support self-administration has not been investigated. Based on the differential effects of lobeline and nicotine in behavioral studies, it appears that these drugs may not be acting via a common CNS mechanism, even though lobeline is often considered to be a nicotinic agonist (Decker et al., 1995).

The positive reinforcing effect of nicotine is believed to be due to the activation of central dopaminergic systems (Bowell and Balfour, 1992; Corrigal et al., 1992, 1994). Presynaptic nicotinic receptors have been found on dopamine (DA)-containing nerve terminals (Giorguieff-Chesselet et al., 1979; Clarke and Pert, 1985). Nicotine binds to nicotinic receptors with high affinity (Kd=1–7 nM) (Lippiello and Fernandes, 1986; Reavill et al., 1988; Romm et al., 1990; Bhat et al., 1991; Loiacono et al., 1993; Anderson and Arneric, 1994). Also, lobeline has been reported to displace [$^3$H]nicotine binding from central nicotinic receptors with high affinity (Ki=5–30 nM) (Yamada et al., 1985; Lippiello and Fernades, 1986; Banerjee and Abood, 1989; Broussolle et al., 1989).

Chronic treatment with nicotine results in an increase in the number of nicotinic receptors in many regions of rat and mouse brain (Collins et al., 1990; Bhat et al., 1991, 1994; Marks et al., 1992; Sanderson et al., 1993). An increase in the number of nicotinic receptors in postmortem human brain tissue obtained from smokers also has been reported (Benwell et al., 1988). In contrast, chronic lobeline administration did not increase the number of nicotinic receptors in mouse brain regions in which increases were observed following chronic nicotine administration (Bhat et al., 1991).

Nicotine evokes DA release in in vitro superfusion studies using striatal slices (Westfall, 1974; Giorguieff-Chesselet et al., 1979; Westfall et al., 1987; Harsing et al., 1992) and striatal synaptosomes (Chesselet, 1984; Rowell et al., 1987; Rapier et al., 1988, 1990; Grady et al., 1992, 1994; Rowell and Hillebrand, 1992, 1994; Rowell, 1995), and in in vivo studies using microdialysis in striatum (Imperato et al., 1986; Damsma et al., 1989; Brazell et al., 1990; Toth et al, 1992). Nicotine-evoked DA release is calcium-dependent, mecamylamine-sensitive and mediated by nicotinic receptors (Giorguieff-Chesselet et al., 1979; Westfall et al, 1987; Rapier et al., 1988; Grady et al., 1992). Mecamylamine is a noncompetitive nicotinic receptor antagonist, which more effectively blocks the ion channel of the receptor (Varanda et al., 1985; Loiacono et al., 1993; Peng et al., 1994). Similar to nicotine, lobeline has been reported to increase DA release from superfused rat and mouse striatal synaptosomes (Sakurai et al., 1982; Takano et al, 1983; Grady et al., 1992). Based on these neurochemical studies, lobeline was suggested to be an agonist at nicotinic receptors. It is difficult to reconcile that nicotine and lobeline similarly release DA and displace [$^3$H]nicotine binding; however, the observed upregulation of nicotinic receptors following chronic nicotine administration is not observed following chronic lobeline administration.

Earlier studies of the pharmacokinetic properties of lobeline have centered on its proposed use in the treatment of nicotinism. For example, U.S. Pat. Nos. 5,536,503; 5,486,362; 5,403,595; and PCT Publication WO 92/19241 are all related to a drug delivery system and method for treating nicotine dependence. U.S. Pat. Nos. 5,414,005; 4,971,079; and 3,901,248 also discuss the use of lobeline in the context of treating nicotine abuse and/or addiction. A scientific article has studied the actions of morphine, lobeline, and other drugs in inducing "analgesia" in rats (S. Hamann et al. 1994). However, these workers did not equate their finding of an "analgesic" response for lobeline to a reduction of the pain response in man, nor did they propose the use of lobeline in treating drug abuse, withdrawal from addiction, and the like.

Similarly, to the present inventors' knowledge, the use of lobeline in the treatment of eating disorders has not been proposed. This is in spite of the widely accepted ability of nicotine to suppress appetite (see, e.g., Remington's Pharm. Sci., 18th ed., p.891) and the previously proposed association of obesity with reduced bioavailability of dopamine (U.S. Pat. Nos. 5,552,429; 5,576,321; 5,272,144; and 5,468, 755).

SUMMARY OF THE INVENTION

In its broadest aspect, the present invention is for a method of treating an individual for drug dependence, withdrawal from drug dependence, or for an eating disorder. The method comprises administering to the individual an amount of a lobeline compound, i.e., lobeline, analogs, and derivatives thereof, including pharmaceutically acceptable salts. The amount of lobeline compound administered is effective to reduce the individual's desire for the drug of abuse or for food. The lobeline compound can be administered alone, combined with an excipient, or coadministered with a second drug having a similar or synergistic effect. The compound or composition is preferably administered subcutaneously, intramuscularly, intravenously, transdermally, orally, intranasally, or rectally.

The utility of lobeline, analogs, and derivatives thereof, e.g., those that form lobeline upon metabolism by the body, in treating dependencies on drugs of abuse is implicated by the present studies. In particular, the treatment of dependencies on such drugs as cocaine, amphetamines, caffeine, phencyclidine, opiates, barbiturates, benzodiazepines, cannabinoids, hallucinogens, and alcohol is implicated. Also, the treatment of eating disorders, such as obesity, is implicated.

In a preferred aspect of the invention, the method of treatment reduces an individual's desire for the drug of abuse or for food by at least one day. It is also preferred that the treatment method further comprise administering behavior modification counseling to the individual.

Although a lobeline compound of the present invention is contemplated primarily for use in the treatment of drug abuse and withdrawal, and for eating disorders, other uses are also suggested by the studies discussed herein. Thus, cognitive disorders, brain trauma, memory loss, psychosis, sleep disorders, obsessive-compulsive disorders, panic disorders, and related conditions are considered to be susceptible to treatment with a lobeline compound of the present invention.

As shown by the results of the studies described herein, and contrary to conventional belief, lobeline is found to act at higher concentrations primarily not as a nicotinic agonist, but by a different mechanism than is observed for nicotine. While not wishing to be bound by any particular theory, it is believed that the lipophilic nature of lobeline permits it to diffuse passively into neurotransmitter-containing vesicles of cells found in the central nervous system (CNS), where it is effective in inducing the release of intracellular dopamine. The present studies also suggest that lobeline may be effective in inhibiting uptake of extracellular dopamine by cells of the CNS, perhaps by blocking dopamine receptors on the cells. Either or both mechanisms can thereby work to increase the extracellular concentration of dopamine. Many respects in which the actions of lobeline are similar to those of amphetamine have been identified.

BRIEF DESCRIPTION OF THE FIGURES

FIG. 2A illustrates the time course of the fractional release evoked by low concentrations (0.01–3 $\mu$M) of lobeline, and FIG. 2B illustrates that evoked by high concentrations (3–100 $\mu$M). *$P<0.05$, different from basal outflow; +$P<0.05$, different from the peak responses at 25 min for 0.01–3 $\mu$M and 30–300 $\mu$M; § $P<0.05$, different from the peak responses of 0.01–10 $\mu$M and 100 $\mu$M; # $P<0.05$, different from the peak responses of 0.01–30 $\mu$M; Fisher's LSD post hoc test. n=6 rats.

DETAILED DESCRIPTION OF THE INVENTION

As used herein, the term "lobeline" refers to a compound having the general chemical formula 2-[6-(β-hydroxyphenethyl)-1-methyl-2-piperidyl]-acetophenone. The term "lobeline" as used herein refers to the above compound in its free form, or as a salt thereof, which has the physiological activity addressed. Inasmuch as a compound having this formula has three chiral centers, eight optical isomers of the compound can exist. However, particular optical isomer(s) are not intended herein unless specifically mentioned.

The term "lobeline analogs" and equivalents thereof, as used herein, refers to chemical derivatives of lobeline, such as those obtained by oxidation or reduction of lobeline, others obtained by esterification of lobeline and its redox derivatives, as well as various substitutions at the N-position of the piperidinyl group in the lobeline molecule.

Preferred lobeline analogs,, which may act as prodrugs of lobeline itself when metabolized by the body, include those contemplated by formula (I) (without regard to chirality):

where R$^1$ and R$^2$ each independently represents hydrogen, lower alkyl, lower alkenyl, lower alkylcarbonyl, arylcarbonyl, aralkylcarbonyl, lower alkoxycarbonyl, lower alkylaminocarbonyl, higher alkylcarbonyl, and poly(alkyleneoxide)carbonyl; R$^3$ and R$^4$ each independently represents hydrogen or combines with R$^1$ and R$^2$, respectively, to form a double bond; and X represents H or lower alkyl. Whenever a carbonyl-containing substituent is provided as R$^1$ or R$^2$, it is understood that the carbonyl group is covalently bonded to the respective O atom appearing in formula (I). Thus, in the instances where the substituent is an alkoxycarbonyl or alkylaminocarbonyl, a carbonate or carbamate linkage is present in the molecule.

Preferred substituents for R$^1$ and R$^2$ include methylcarbonyl (acetyl), phenylcarbonyl (benzoyl), natural fatty acid groups, e.g., palmitoyl, oleyl, linoleyl, stearyl, and lauryl, and polyethyleneglycol (PEG) covalently bonded to the molecule via a carbonate linkage. Long chain moieties such as a PEG group in a lobeline prodrug enhance transdermal delivery of the molecule, which may be metabolized to lobeline and derivatives thereof.

As used herein, the terms "lower alkyl", "lower alkenyl", "lower alkoxy", and the like, refer to normal, branched and cyclic hydrocarbyl groups containing 1 to 6 carbon atoms. The term "higher alkyl" includes alkyl groups containing 7 to about 20 carbon atoms. The term "aryl" refers to a hydrocarbon group containing one or more aromatic rings, optionally substituted with one or more heteroatoms. The term "aralkyl" refers to an aryl group covalently bonded to a lower alkyl group.

It is, of course, contemplated that certain lobeline analogs having the above formula may be converted into a different molecule upon metabolism by the body. For example, whenever an acetyl group is present at R$^1$ and/or R$^2$ in the compound, the acetyl group may be removed by metabolic processes, e.g., such as occur in the gastrointestinal tract or the liver. The choice of substituents is subject to considerations of toxicity, side effects, dosage, and the like.

Particularly preferred lobeline analogs are those in which (i) both R$^1$ and R$^2$ are H (i.e., a lobelanidine compound), (ii) either R$^1$ or R$^2$ is H and the other combines with R$^3$ or R$^4$ to form a double bond (i.e., a lobeline compound), and (iii) both R$^1$ and R$^2$ combine with either R$^3$ or R$^4$ to form a double bond (i.e., a lobelanine compound). It is also preferred that X in the above formula represents a methyl group. Preferably, the chirality at the 2 and 6 positions of the piperidyl ring of the compounds is the same as in naturally occurring lobeline.

Lobeline, as well as analogs thereof, can be administered in its free base form or as a soluble salt. Whenever it is desired to employ a salt of lobeline or analog, it is preferred that a soluble salt be employed. Some preferred salts include the hydrochloride, hydrobromide, nitrate, sulfate, tartrate, fumarate, citrate, maleate, ascorbate, lactate, aspartate, mesylate, benzene sulfonate, propionate and succinate salts. Also, other anionic moieties such as fatty acid salts can be used, e.g., palmitate salt.

As used herein, an "effective amount", and similar usages, refers to an amount of a drug effective to reduce an individual's desire for a drug of abuse, or for food.

A pharmaceutical composition containing a lobeline compound of the invention is also contemplated, which may include a conventional additive such as a stabilizer, buffer, salt, perservative, filler, flavor enhancer, and the like, as known to those skilled in the art. Representative buffers include phosphates, carbonates, citrates, and the like. Exemplary preservatives include EDTA, EGTA, BHA, BHT, and the like.

A composition of the invention may be administered by inhalation, i.e., intranasally as an aerosol or nasal formulation; topically, i.e., in the form of an ointment, cream or lotion; orally, i.e., in solid or liquid form (tablet, gelcap, time release capsule, powder, solution, or suspension in aqueous or non-aqueous liquid); intravenously as an infusion or injection, i.e., as a solution, suspension, or emulsion in a pharmaceutically acceptable carrier; transdermally, e.g., via a transdermal patch; rectally, as a suppository, and the like.

Generally, it is expected that a pharmacologically effective dose of a present compound will require its administration in an amount less than $1\times10^{-3}$ mg/kg of body weight per day. The amount to be administered depends to some extent on the lipophilicity of the specific compound selected, since it is expected that this property of the compound will cause it to partition into fatty deposits of the subject. The precise amount to be administered can be determined by the skilled practitioner in view of desired dosages, side effects, the medical history of the patient, and the like. It is anticipated that the compound will be administered in an amount ranging from about $1\times10^{-5}$ to about $1\times10^{-3}$ mg/kg/day.

The present study was performed to determine the involvement of nicotinic receptors in lobeline-evoked [$^3$H] overflow from rat striatal slices preloaded with [$^3$H]DA. The calcium-dependency of the effect of lobeline and the ability of mecamylamine to inhibit the lobeline response were determined. To assess the contribution of potential effects on DA uptake, the effect of nicotine and lobeline to inhibit [$^3$H]DA uptake into striatal synaptosomes and synaptic vesicle preparations was also determined. Based on the present results of the in vitro superfusion studies, striatal dopamines (DA) and dihydroxy phenylacetic acid (DOPAC) content were also determined after lobeline superfusion in vitro, and after lobeline administration in vivo.

Effect of nicotine on superfused rat striatal slices preloaded with [$^3$H]DA

Figure 1A:
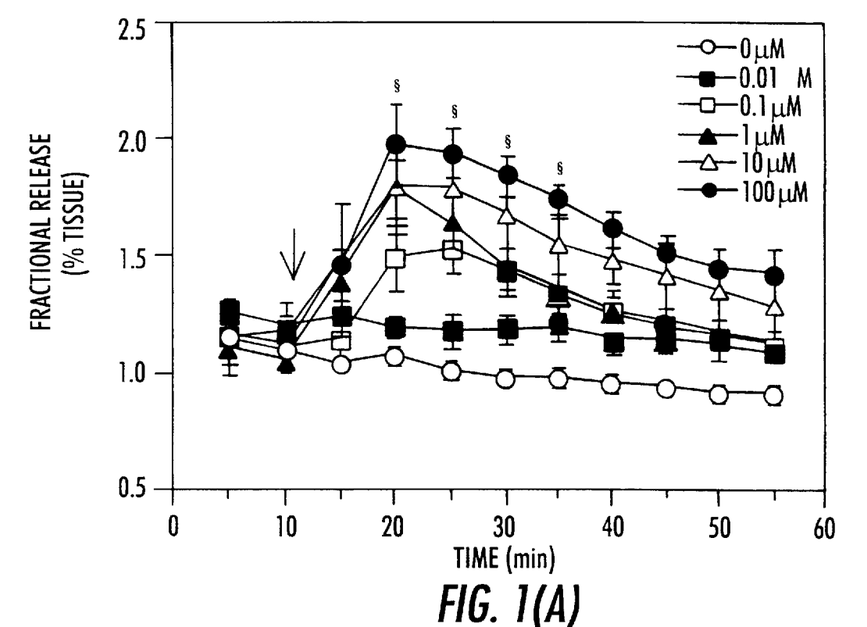
FIGS. 1(A) and 1(B) depicts the time course of nicotine-evoked fractional release (A) and concentration-dependence of nicotine-evoked total [$^3$H]overflow (D) from rat striatal slices preloaded with [$^3$H]DA (3,4-dihydroxyphenylethyl-2-[N-$^3$H]-amine). Nicotine was added to the superfusion buffer after the second sample (as indicated by the arrow) and remained in the buffer until the end of the experiment. The data in FIG. 1A are presented as means±S.E. fractional release, which represents the tritium in the sample as a percentage of the total tritium in the slice at the time of sample collection. The data in FIG. 1B are presented as mean±S.E. total [$^3$H]overflow, which represents the area under the curve of the corresponding nicotine concentration-response as a function of time. § $P<0.05$, different from basal (5–10 min), when fractional release was collapsed across nicotine concentration; *$P<0.05$, significantly different from 0–0.01 $\mu$M and 1–100 $\mu$M; $P<0.05$, different from 0–0.1 $\mu$M and 100 $\mu$M; *$P<0.05$, different from 0–10 $\mu$M; Duncan's New Multiple Range Test. n=4–9 rats.

In a concentration-dependent manner, nicotine evoked an increase in the fractional release of tritium over the time course of the superfusion experiment (FIG. 1A). Repeated-measures, two-way ANOVA (analysis of variants) revealed a significant main effect of nicotine concentration ($F_{(8,429)}=29.45$, $P<0.0001$) and a significant main effect of time ($F_{(10,429)}=9.76$, $P<0.0001$), but the concentration×time interaction was not significant ($F_{(80,420)}=1.22$, $P>0.05$). Fractional release peaked within 10–15 min after the addition of nicotine to the superfusion buffer. From 10–25 min after the addition of nicotine, fractional release was significantly increased above basal outflow, when the data were collapsed across nicotine concentration. At peak fractional release, the highest concentration of nicotine examined increased fractional release 2-fold above basal. Furthermore, when the data were collapsed across nicotine concentration, fractional release, from 30–45 min after nicotine addition, was not significantly different from basal, despite the presence of nicotine in the superfusion buffer throughout the superfusion period.

Figure 1B:
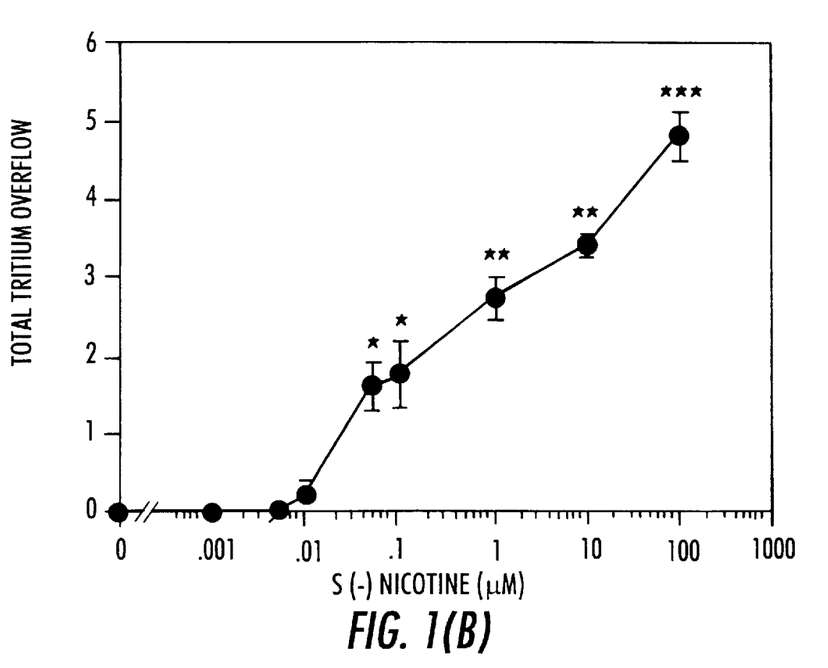

Presentation of the results as nicotine-evoked total [$^3$H] overflow accentuates the concentration-dependent nature of the response to nicotine (FIG. 1B). Repeated-measures, one-way ANOVA revealed a significant nicotine-concentration effect ($F_{(8,39)}=25.77$, $P<0.0001$). The lowest nicotine concentration which evoked a significant increase in [$^3$H]overflow was 0.05 $\mu$M. A plateau in the concentration-response curve was not apparent over the concentration range examined. Higher concentrations of nicotine were not examined because of the extensive work of Westfall and collaborators (Westfall, 1974; Westfall et al., 1987) indicating that nicotine concentrations higher than 100 $\mu$M act to release DA from superfused rat striatal slices by a mechanism which is not calcium-dependent nor nicotinic-receptor mediated.

Effect of lobeline on superfused rat striatal slices preloaded with [$^3$H]DA

Figure 2A:
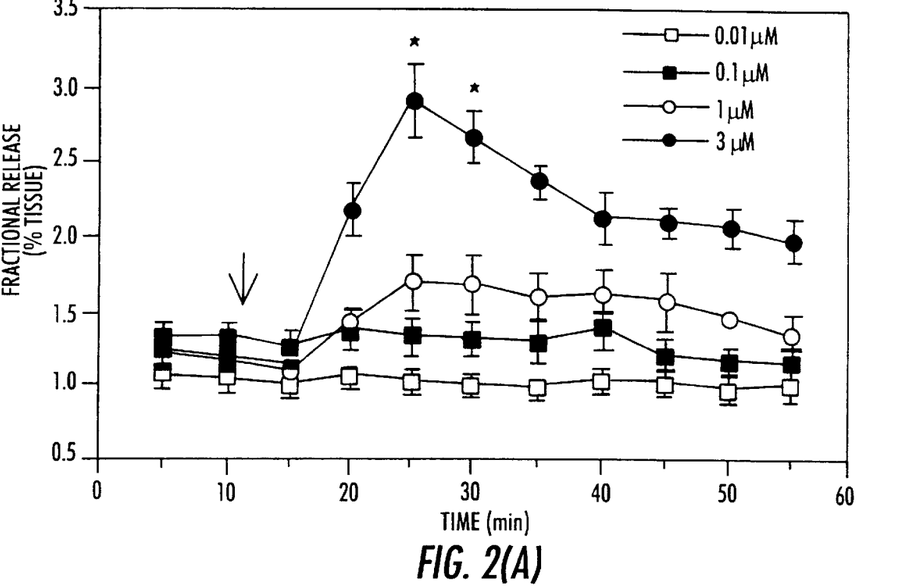
FIGS. 2(A) and 2(B) depict the time course of lobeline-evoked fractional release from rat striatal slices preloaded with [$^3$H]DA. Lobeline was added to the superfusion buffer after the collection of the second sample (as indicated by the arrow) and remained in the buffer until the end of the experiment. Data are presented as mean±S.E. fractional release, which represents the tritium in the superfusate sample as a percentage of the total tritium in the slice at the time of sample collection.
Figure 2B:
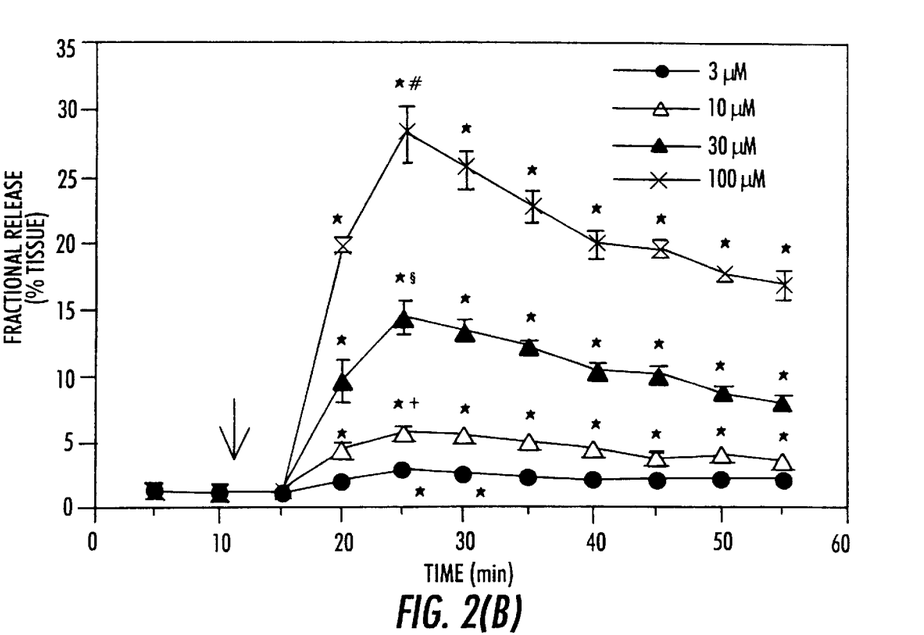

Lobeline evoked a marked concentration-dependent increase in fractional release of tritium over the time course of the superfusion experiment (FIG. 2). Repeated-measures, two-way ANOVA revealed a significant main effect of lobeline concentration ($F_{7,363}=1057.13$, $P<0.0001$), a significant main effect of time ($F_{(10,363)}=132.24$, $P<0.0001$) and a significant concentration×time interaction ($F_{(70,363)}=44.85$, $P<0.0001$). Low concentrations (0.01–1 $\mu$M) of lobeline did not significantly increase fractional release during the entire superfusion period. Lobeline (3 $\mu$M) evoked a significant increase in fractional release 15 and 20 min after its addiction to the buffer. Subsequently, the fractional release returned towards basal, despite the continuous presence of lobeline in the buffer. Fractional release evoked by high concentrations (10–100 $\mu$M) of lobeline was significantly increased 10 min after the addition of lobeline to the buffer and remained significantly higher than basal until the end of the experiment.

Of note is the magnitude of the response to lobeline in comparison to that observed after superfusion with nicotine. Peak fractional release after superfusion with 30 and 100 $\mu$M lobeline was approximately 15% and 30%, respectively, of the total tritium present in the striatal slice (FIG. 2B). Furthermore, over the remainder of the superfusion period, fractional release in superfusate samples continued to be 10–20% of the total tritium in the slice. On the other hand, peak fractional release induced by the highest concentration (100 $\mu$M) of nicotine was only 2% of total tritium in the slice, and fractional release returned to basal during the course of the experiment (FIG. 1A). These results suggest the potential for depletion of DA storage pools following superfusion with lobeline at high concentrations.

Figure 3:
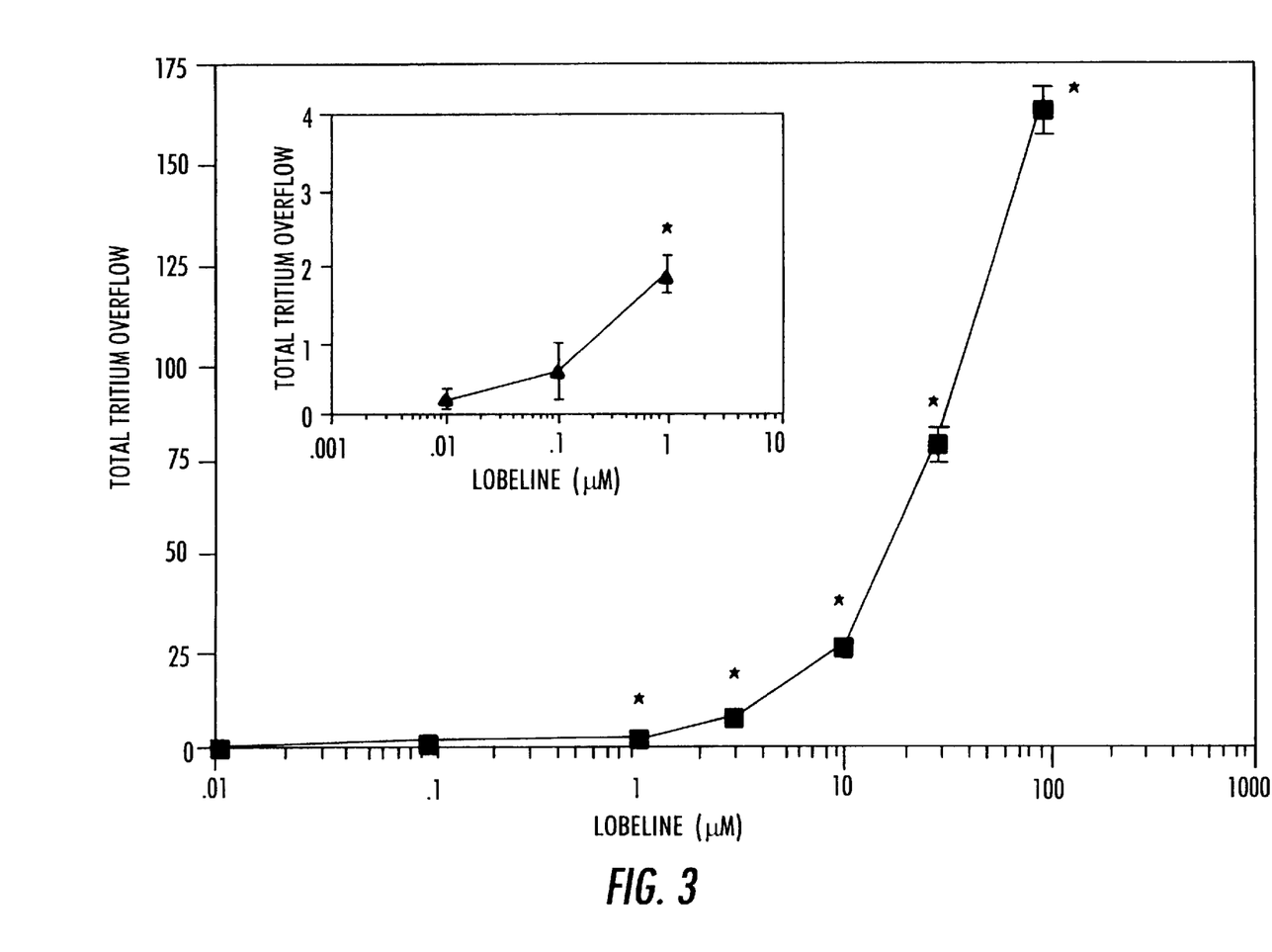
FIG. 3 depicts the concentration-dependence of lobeline-evoked total [$^3$H]overflow from rat striatal slices preloaded with [$^3$H]DA. Data are presented as mean±S.E. total [$^3$H] overflow, which represents the area under the curve of the corresponding lobeline concentration-response as a function of time. The inset illustrates the total [$^3$H]overflow evoked by the lower concentrations (0.01–1 $\mu$M) of lobeline. Control slices which were superfused with buffer in the absence of lobeline did not evoke [$^3$H]overflow (i.e. fractional release was not different from basal during the course of superfusion). * $P<0.05$, different from control and each of the other lobeline concentrations; Duncan's New Multiple Range Test. n=6 rats.

Expression of the results as total [$^3$H]overflow also revealed a concentration-dependent effect of lobeline and a marked increase in [$^3$H]overflow evoked by high concentrations of lobeline (FIG. 3). Repeated-measures, one-way ANOVA revealed a significant lobeline concentration effect ($F_{(6,35)}=61.55$, $P<0.0001$). The lowest concentration of lobeline to evoke a significant increase in total [$^3$H]overflow was 1 $\mu$M. As the lobeline concentration was increased, a significantly greater total [$^3$H]overflow was evoked. Furthermore, a plateau in the concentration-response curve was not apparent over the concentration range examined.

Lobeline-induced [$^3$H]overflow: Lack of calcium-dependency

Previous studies (Westfall, 1974; Westfall et al., 1987) reported that nicotine (<100 $\mu$M)-evoked [$^3$H]overflow from rat striatal slices preloaded with [$^3$H]overflow was calcium-dependent. In order to determine if lobeline-induced [$^3$H] overflow was calcium-dependent, the effect of lobeline was determined in a calcium-free superfusion buffer containing 0.5 mM EGTA (ethylene glycol-bis($\beta$-aminoethyl ether)-N, N,N',N'-tetraacetic acid (See Table 1). Two-way ANOVA revealed a significant main effect of lobeline concentration (within-group factor, $F_{(3,39)}=473.08$, $P<0.001$), however, the main effect of inclusion of calcium in the buffer was not significant (between-groups factor, $F_{(1,39)}=0.13$, $P>0.05$) and the interaction term also was not significant ($F_{(3,39)}=1.64$, $P>0.05$). Thus, the effect of lobeline on [$^3$H]overflow was not altered following removal of calcium from the superfusion buffer.

TABLE 1

Lobeline Evokes [$^3$H]Overflow from Rat Striatal Slices Preloaded with [$^3$H]DA in a Calcium-Independent Manner*

| Lobeline Concentration ($\mu$M) | Control Buffer | Calcium-Free Buffer |
|---|---|---|
| 0.1 | 0.6 ± 0.4 | 0 ± 0 |
| 1 | 2.0 ± 0.6 | 2.9 ± 0.2 |
| 10 | 31.9 ± 2.2 | 45.0 ± 4.2 |
| 100 | 198.0 ± 20 | 185.0 ± 12.0 |

*Concentration-response of lobeline was determined using either control Krebs' buffer or calcium-free buffer with the addition of 0.5 mM EGTA. Data are presented as mean ± S.E. total [$^3$H]overflow, n = 6 rats/group.

Nicotine-evoked and lobeline-evoked [$^3$H]overflow: mecamylamine antagonism

In a concentration-dependent manner, mecamylamine significantly inhibited nicotine (10 $\mu$M)-evoked [$^3$H]overflow from rat striatal slices preloaded with [$^3$H]DA (See Table 2). Repeated-measures, one-way ANOVA revealed a significant mecamylamine concentration effect ($F_{(5,38)}$=4.46, P<0.005). Concentrations of mecamylamine from 0.1–100 $\mu$M inhibited (57%–91%) the effect of nicotine to evoke [$^3$H] overflow.

Figure 4:
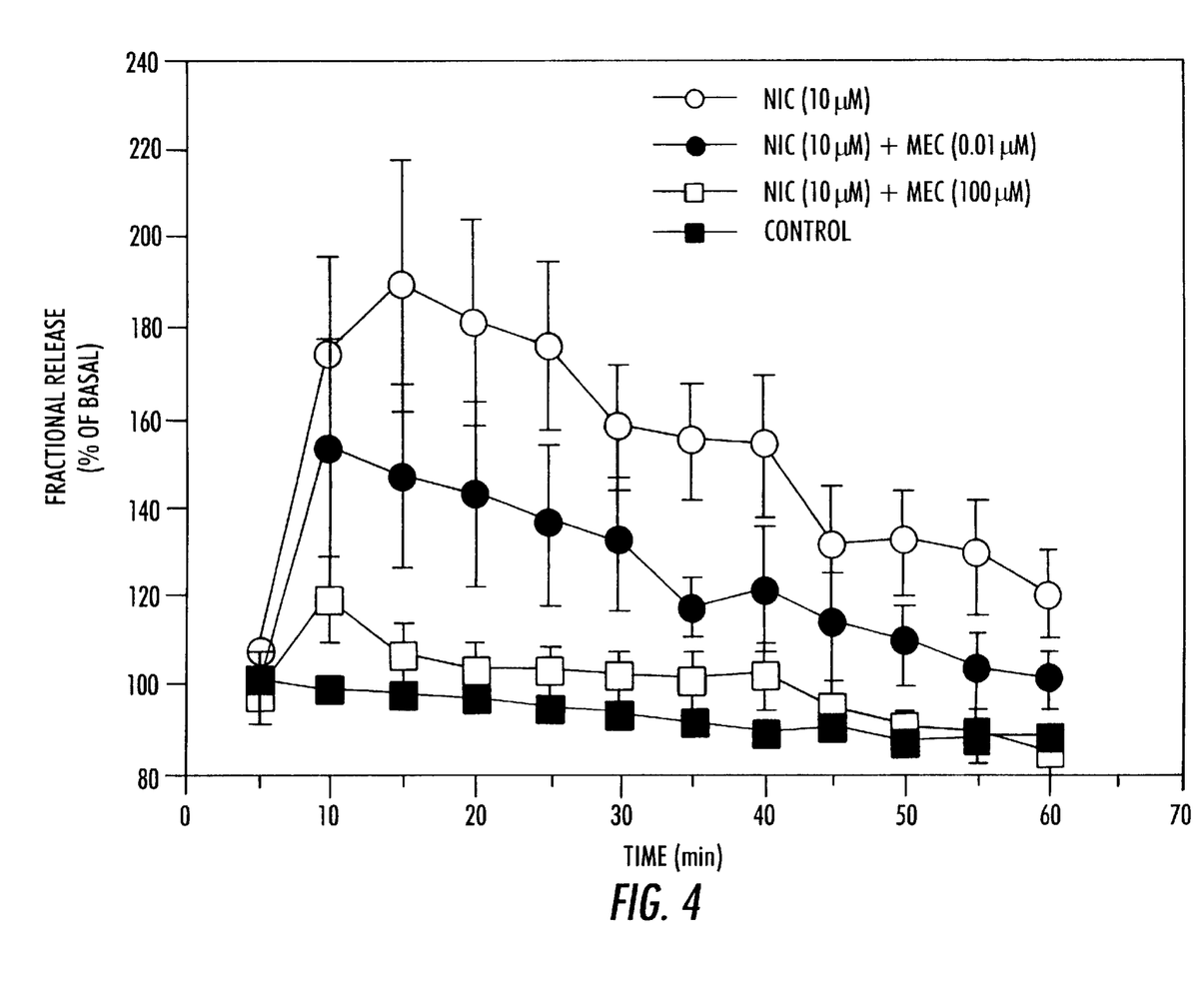
FIG. 4 depicts the time course of the effect of mecamylamine to inhibit nicotine (10 $\mu$M)-evoked fractional release of [$^3$H]DA from preloaded rat stratal slices. For clarity of graphical presentation, only significant effects of the lowest and highest concentration, 0.01 and 100 $\mu$M, respectively, of mecamylamine are illustrated. Data are presented as mean±S.E. fractional release as percentage of basal outflow. Experiments were performed as described in Table 2 hereinbelow. The time course begins at the time of nicotine (10 $\mu$M) addition to the superfusion buffer containing mecamylamine. The control represents fractional release in the absence of either mecamylamine or nicotine in the superfusion buffer. Duncan's New Multiple Range Test revealed a significant inhibitory effect of 0.01 μM mecamylamine, when the data were collapsed across time of superfusion. n=8 rats.

The time course of the effect of mecamylamine illustrates the pattern and the extent of the inhibition of the nicotine-evoked increase in fractional release (FIG. 4). Repeated-measures, two-way ANOVA revealed a significant main effect of mecamylamine concentration ($F_{(6,599)}$=19.59, P<0.0001), a significant main effect of time ($F_{(11,599)}$=4.98, P<0.0001), but the concentration×time interaction was not significant ($F_{(66,599)}$=0.97, P>0.05). When the data were collapsed across time, the lowest concentration of mecamylamine to produce a significant inhibition of nicotine's effect was 0.01 $\mu$M. The time course illustrates the small, but significant, inhibition (36%) of nicotine's effect produced by this low concentration of mecamylamine. Interestingly, the inhibitory effect of 0.01 $\mu$M mecamylamine was not detected when the results were expressed as total [$^3$H]overflow (See Table 2). The maximal inhibitory effect of the highest concentration (100 $\mu$M) of mecamylamine is also illustrated in FIG. 4 for comparison.

TABLE 2

Mecamylamine Inhibition of Nicotine (10 $\mu$M)-evoked [$^3$H]Overflow from Rat Striatal Slices Preloaded with [$^3$H]DA*

| Mecamylamine ($\mu$M) | Total [$^3$H]Overflow |
|---|---|
| 0 | 5.60 ± 1.20 |
| 0.01 | 3.57 ± 1.52 |
| 0.1 | 2.40 ± 0.87* |
| 1 | 1.59 ± 0.64** |
| 10 | 1.02 ± 0.43** |
| 100 | 0.54 ± 0.32** |

*Slices were superfused with buffer in the absence or presence of mecamylamine (0.01–100 $\mu$M) for 60 min, followed by 60 min superfusion with the addition of 10 $\mu$M of nicotine to the buffer containing the various concentrations of mecamylamine. Data are presented as mean ± S.E. total [$^3$H] overflow. Total [$^3$H]overflow for slices superfused in the absence of any drug was 0.06 ± 0.06. Slices superfused with nicotine (10 $\mu$M) in the absence of mecamylamine were considered control for statistical analysis.
*P < 0.05, one-tailed, different from control;
**P < 0.05, two-tailed, different from control; Dunnett's post hoc test. n = 8 rats The ability of mecamylamine (1–100 $\mu$M) to inhibit lobeline (0.1–100 $\mu$M)-evoked total [$^3$H]overflow is shown in Table 3. Concentrations of mecamylamine which significantly inhibited nicotine-evoked [$^3$H]overflow were utilized in these experiments. The effect of lobeline (0.1–100 $\mu$M) in the absence of mecamylamine represented control. Two-way ANOVA revealed a significant main effect of lobeline concentration (within groups factor, $F_{(4,56)}$=603.84, P<0.0001); however, both the main effect of mecamylamine concentration (between-groups factor, $F_{(3,14)}$=2.79, P>0.05) and the lobeline×mecamylamine interaction were not significant ($F_{(12,56)}$=1.30, P>0.05). Thus, lobeline-evoked [$^3$H]overflow was not inhibited by mecamylamine.

TABLE 3

Lobeline-evoked [$^3$H]Overflow from Rat Striatal Slices Preloaded with [$^3$H]DA is Not Inhibited by Mecamylamine*

| Mecamylamine Concentration ($\mu$M) | Lobeline Concentration ($\mu$M) | | | | |
|---|---|---|---|---|---|
| | 0.1 | 1 | 3 | 10 | 100 |
| 0 | 0.6 ± 0.4 | 2.0 ± 0.6 | 10.3 ± 0.8 | 31.9 ± 2.2 | 185.0 ± 12 |
| 1 | 0.9 ± 0.5 | 4.9 ± 1.8 | 10.8 ± 1.4 | 32.5 ± 1.0 | 180.0 ± 47.6 |
| 10 | 0.8 ± 0.3 | 2.4 ± 0.5 | 8.2 ± 1.5 | 41.0 ± 6.2 | 179.5 ± 12.2 |
| 100 | 0.5 ± 0.4 | 0.7 ± 0.1 | 6.5 ± 0.9 | 20.0 ± 2.0 | 160.4 ± 30.2 |

*Slices were superfused with buffer in the absence or presence of mecamylamine (1–100 $\mu$M) for 60 min, followed by 60 min superfusion with the addition of lobeline (0.1–100 $\mu$M) to the buffer. Data are presented as mean ± S.E. total [$^3$H]overflow. n = 4–6 rats.

Figure 5:
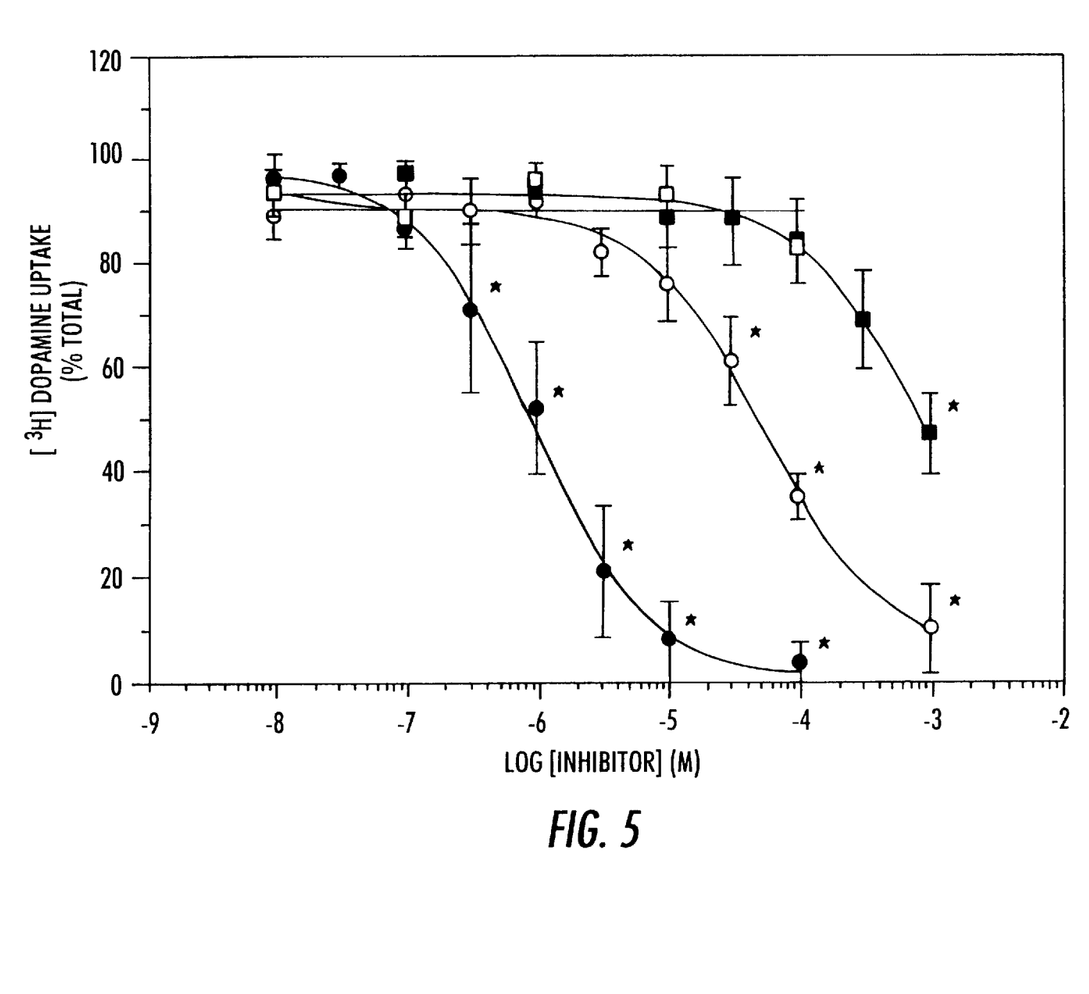
FIG. 5 depicts the effects of nicotine (0.01–1000 μM) and lobeline (0.01–1000 μM) on rat striatal synaptosomal and synaptic vesicular [$^3$H]DA uptake. □ nicotine, synaptosomal [$^3$H]DA uptake; ■ nicotine, vesicular [$^3$H]DA uptake; ○ lobeline, synaptosomal [$^3$H]DA uptake; ● lobeline, vesicular [$^3$H]DA uptake. Data are presented as mean±S.E. percentage of total [$^3$H]DA uptake. Total [$^3$H]DA uptake for synaptosomes and vesicles was 109±9.80 pmol/min/mg and 1340±71.7 pmol/min/mg, respectively. Non-specific [$^3$H]DA uptake in synaptosomal and vesicular experiments was 2% and 20%, respectively, of total [$^3$H]DA uptake as determined by incubation with 10 μM GBR and incubation at 0° C., respectively. Experiments examining the effect of nicotine on synaptosomal uptake included a low concentration range (0.001–1 nM), however, no effect was observed and for clarity of graphical presentation these results are not illustrated. *P<0.05, different from total [$^3$H]DA uptake; Dunnett's post hoc test. n=3–6 rats.

The effect of nicotine and lobeline on [$^3$H]DA uptake into rat striatal synaptosomes and synaptic vesicles To determine if modulation of DA uptake contributed to the increase in [$^3$H]overflow evoked by nicotine or lobeline, [$^3$H]DA uptake into striatal synaptosomes and synaptic vesicles was determined (FIG. 5). Nicotine did not inhibit [$^3$H]DA uptake into striatal synaptosomes over the concentration range (0.001 nM–100 $\mu$M) examined. Before determining the effect of nicotine on synaptic vesicular [$^3$H]DA uptake, the purity of the isolated synaptic vesicle preparation was determined by electron microscopy of representative vesicle preparations. Plain spheroid or ellipsoid synaptic vesicle profiles of approximately 50 nm in diameter were the predominant membrane structures observed. Very few ($\leq$1%) contaminating membrane fragments were present. The effect of nicotine on [$^3$H]DA uptake into synaptic vesicles was analyzed by repeated-measures, one-way ANOVA which revealed a significant nicotine concentration effect ($F_{(9,28)}$=3.30, P<0.05). However, Dunnett's post hoc analysis revealed that significant inhibition of uptake only occurred at very high concentration (1 mM) of nicotine.

Lobeline inhibited [$^3$H]DA uptake into synaptopsomes in a concentration-dependent manner (FIG. 5). Repeated-measures, one-way ANOVA revealed a significant lobeline concentration effect ($F_{(9,38)}$=154.0, P<0.0001). The lowest concentration of lobeline to produce a significant inhibition in the synaptosomal preparation was 30 $\mu$M. The IC$_{50}$ for lobeline to inhibit uptake into synaptosomes was 80±12 $\mu$M. Moreover, in contrast to nicotine, lobeline potently inhibited [$^3$H]DA uptake into synaptic vesicles in a concentration-dependent manner ($F_{8,26}$=28.60, P<0.0001). The lowest concentration of lobeline to produce a significant inhibition was 0.3 $\mu$M, and complete inhibition was obtained at 10 $\mu$M. The IC$_{50}$ value for lobeline to inhibit vesicular uptake was 0.88±0.001 $\mu$M, which was 2-orders of magnitude lower than that for lobeline-induced inhibition of synaptosomal [$^3$H]DA uptake. Tetrabenazine (0.001–100 $\mu$M), a high affinity and specific inhibitor of the synaptic vesicular monoamine transporter, significantly inhibited striatal vesicular [$^3$H]DA uptake in a concentration-dependent manner ($F_{(9,28)}$=23.78, P<0.0001). The $IC_{50}$ for tetrabenazine was 77.7±1.3 nM, and the lowest concentration of tetrabenazine which significantly inhibited vesicular uptake was 0.07 μM. Complete inhibition was obtained at 1 μM tetrabenazine. Thus, lobeline was approximately one order of magnitude less potent than tetrabenazine in inhibiting vesicular [$^3$H]DA uptake.

Effect of lobeline on endogenous DA and DOPAC content in rat striatum

Figure 6:
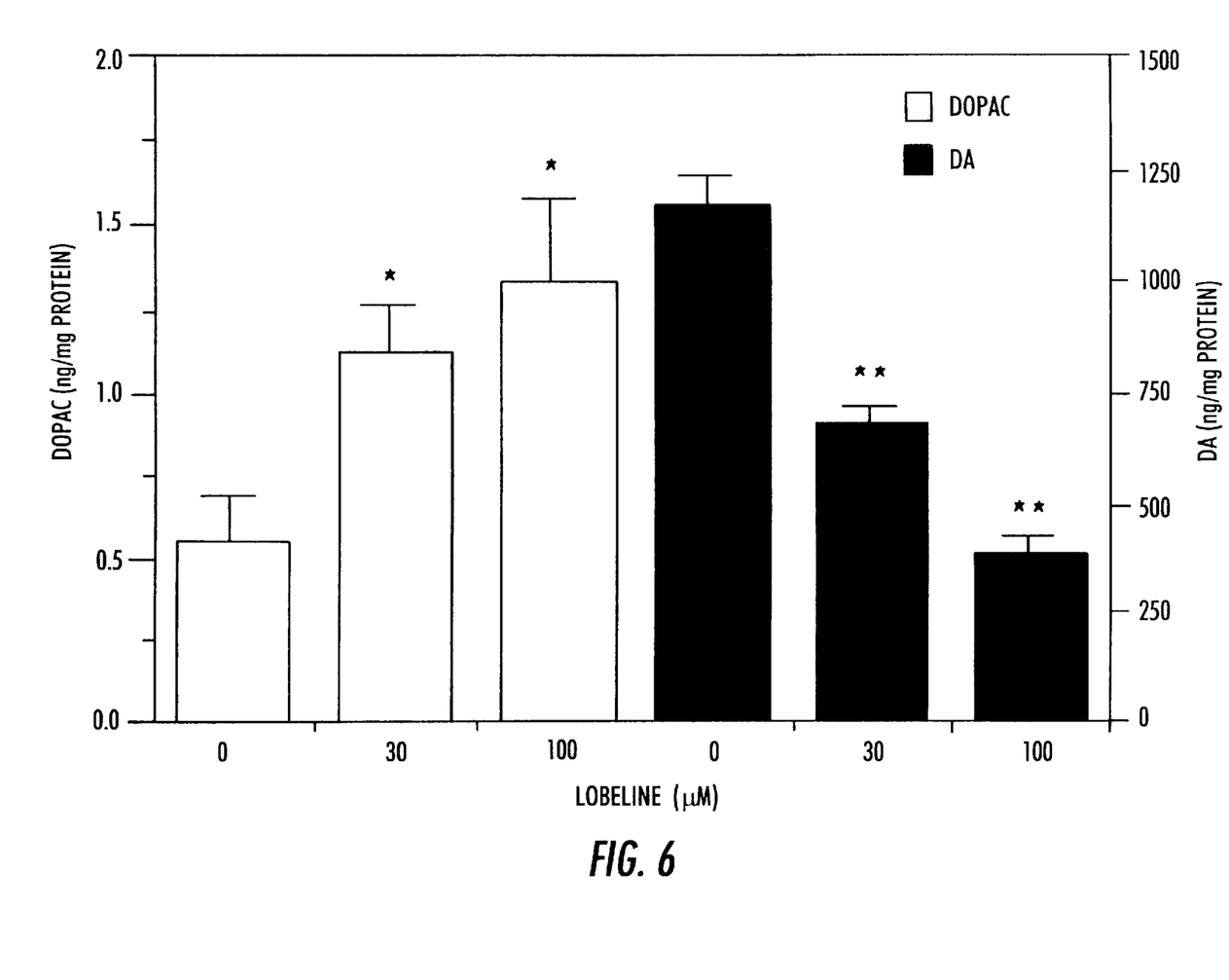
FIG. 6 depicts the endogenous DA and DOPAC (dihydroxyphenylacetic acid) content in rat striatal slices superfused with high concentrations (30–100 μM) of lobeline. Endogenous DA and DOPAC content were determined after 60 min superfusion with various concentrations of lobeline. Data are presented as mean±S.E. ng/mg protein. *P<0.05, different from control, P<0.05, **P<0.001, different from control; Dunnett's post hoc test. n=8 rats.

The marked increase in [$^3$H]overflow in response to superfusion with high concentrations of lobeline (FIGS. 2 and 3) and the lobeline-induced inhibition of synaptosomal and vesicular [$^3$H]DA uptake (FIG. 5) suggested that superfusion with lobeline may deplete striatal DA content. One-way ANOVA revealed a significant lobeline concentration effect on DA ($F_{(6,41)}$=15.35, P< 0.0001) and DOPAC ($F_{(6,40)}$=6.90, P<0.0001) content in superfused striatal slices. Superfusion with low concentrations (0.1–10 μM) of lobeline did not alter DA or DOPAC content (data not shown); however, when slices were superfused with high lobeline concentrations (30–100 μM), lobeline significantly depleted endogenous DA content and increased DOPAC content compared to a control (FIG. 6).

To determine if lobeline-induced depletion of endogenous DA content occurred after in vivo administration of lobeline to rats, lobeline was administered (s.c.) acutely (0, 1, 3, 10, 30 mg/kg), intermittently (0, 3, 10 mg/kg, once daily for days) or continuously (0, and 30 mg/kg, by osmotic minipump delivery for 21 days), and rat striata were obtained for the determination of endogenous DA and DOPAC content (See Table 4). Two-way ANOVA revealed that lobeline did not significantly alter either striatal DA ($F_{(4,58)}$=0.05, P>0.05) or DOPAC ($F_{(4,58)}$=0.54, P>0.05) content. Therefore, lobeline administration in vivo did not deplete striatal DA content at any dose of lobeline or any treatment regimen examined.

TABLE 4

In vivo Administration of Lobeline Does Not Alter DA and DOPAC Content in Rat Striatum*

| | Lobeline (mg/kg) | | | | |
|---|---|---|---|---|---|
| | 0 | 1 | 3 | 10 | 30 |
| DA Acute | 739 ± 64 | 756 ± 111 | 761 ± 103 | 841 ± 76 | 665 ± 126 |
| Intermittent | 743 ± 57 | ND | 778 ± 27 | 800 ± 41 | ND |
| Chronic | 840 ± 72 | ND | ND | ND | 856 ± 144 |
| DOPAC Acute | 84 ± 12 | 81 ± 12 | 89 ± 15 | 82 ± 8 | 72 ± 10 |
| Intermittent | 63 ± 6 | ND | 57 ± 12 | 57 ± 3 | ND |
| Chronic | 61 ± 4 | ND | ND | ND | 62 ± 10 |

*Rat striata were obtained 1 hr after acute lobeline administration (0, 1–30 mg/kg, s.c.); after intermittent lobeline administration (0,3 and 10 mg/kg, once daily injection for 10 days, s.c.); and after chronic lobeline delivery by osmotic minipump (0 and 30 mg/kg/day for 21 days, s.c.). Data are presented as mean ± S.E. ng/mg protein. ND: not determined. n = 6–8 rats/group.

The invention will now be discussed by way of certain examples, which illustrate, but do not limit, the invention.

EXAMPLES

Materials

S(−)Nicotine ditartrate, nomifensine maleate, mecamylamine hydrochloride, and GBR 12909 were purchased from Research Biochemicals, Inc. (Natick, Mass.). Tetrabenazine was purchased from Fluka Chemika-BioChemika (Ronkonkoma, N.Y.). [$^3$H]Dopamine ([$^3$H]DA; 3,4-dihydroxyphenylethyl(2-[N-$^3$H])amine; specific activity, 25.6 Ci/mmol) was purchased from New England Nuclear (Boston, Mass.). Dopamine hydrochloride, 3,4-dihydroxyphenylacetic acid (DOPAC), 3,4-dihydroxybenzylamine hydrobromide (DHBA), lobeline hemisulfate, pargyline hydrochloride, HEPES (N-[2-hydroxyethyl piperazine]-N'-[2-ethanesulfonic acid]), potassium tartrate, adenosine 5'-triphosphate magnesium salt (ATP-$Mg^{2+}$), L(+)tartaric acid and 1-octanesulfonic acid sodium salt were purchased from Sigma Chemical Co. (St. Louis, Mo.). α-D-Glucose and sucrose were purchased from Aldrich Chemical Co., Inc. (Milwaukee, Wis.). Ascorbic acid was purchased from AnalaR (BHD Ltd., Poole, U.K.). Glutaraldehyde, osmium tetroxide and copper grids were purchased from EMS Inc. (Fort Washington, Calif.). Eponate 12 was purchased from Ted Pella, Inc. (Redding, Calif.). TS-2 tissue solubilizer was purchased from Research Products International (Mount Prospect, Ill.). Acetonitrile (HPLC grade) was purchased from EM Science (EM Industries, N.J.). All other chemicals were purchased from Fisher Scientific (Pittsburgh, Pa.).

Subjects

Male Sprague-Dawley rats (200–250 g) were obtained from Harlan Laboratories (Indianapolis, Ind.) and were housed two per cage with free access to food and water in the Division of Lab Animal Resources at the College of Pharmacy at the University of Kentucky. Experimental protocols involving the animals were in strict accordance with the NIH Guide for the Care and Use of Laboratory Animals and were approved by the Institutional Animal Care and Use Committee at the University of Kentucky.

Example 1
In Vivo Administration of Lobeline

For acute administration studies, lobeline (1, 3, 10 and 30 mg/kg) or vehicle (distilled water) was administered subcutaneously (s.c.) acutely, and striata were obtained 1 hr after injection for determination of endogenous DA and DOPAC content. For intermittent chronic administration studies, lobeline (3 and 10 mg/kg) or vehicle was administered s.c. once daily for 10 days. Rats were killed 24 hrs after the last injection and striata were obtained immediately for determination of endogenous DA and DOPAC content. For continuous chronic administration, an osmotic minipump (ALZET 2mL4 model, ALZA Corporation, Palo Alto, Calif.) containing 152 mg/ml of lobeline was implanted s.c. under ether anesthesia. A flow rate of 2.5 μl/hr delivered lobeline (30 mg/kg/day) or vehicle continuously for a 21-day period. Striata were obtained for endogenous DA and DOPAC content determination 21 days after osmotic minipump implantation. Lobeline dose was expressed in terms of mg of lobeline hemisulfate salt per kg body weight.

Example 2
[$^3$H]DA Release Assay

The effect of lobeline and nicotine on [$^3$H]overflow from rat striatal slices preloaded with [$^3$H]DA was determined using a previously published method (Dwoskin and Zahniser, 1986). Rat striata were rapidly dissected on ice and were sliced using a McIlwain tissue chopper. Slices (500 μm, 6–8 μg) were incubated in Krebs' buffer (in mM; 118 NaCl, 4.7 KCl, 1.2 $MgCl_2$, 1.0 $NaH_2PO_4$, 1.3 $CaCl_2$, 11.1 α-D-glucose, 25 $NaHCO_3$, 0.11 L-ascorbic acid, and 0.004 EDTA (ethylenediamine tetraacetic acid), pH 7.4 and saturated with 95% $O_2$/5% $CO_2$) in a metabolic shaker at 34° C. for 30 min to allow for recovery of responsiveness. Slices were rinsed with 15 ml fresh buffer and then incubated in fresh buffer containing 0.1 μM [$^3$H]DA (6–8 slices/3 ml) for an additional 30 min. Subsequently, slices were rinsed with 15 ml fresh buffer and transferred to a glass superfusion chamber. Slices were superfused at 1 ml/min with Krebs' buffer (34° C., pH 7.4, aerated with 95% $O_2$/5% $CO_2$) containing nomifensine (10 $\mu$M), a DA uptake inhibitor, and pargyline (10 $\mu$M), a monoamine oxidase inhibitor, to ensure that [$^3$H]overflow primarily represented [$^3$H]DA, rather than [$^3$H]DA metabolites (Cubeddu et al., 1979; Zumstein et al., 1981; Rapier et al, 1988). After 60 min of superfusion when basal outflow was stabilized, two 5-min samples (5 ml) were collected to determine basal [$^3$H]outflow.

For the nicotine or lobeline concentration-response studies, a single concentration of either nicotine (0.001–100 $\mu$M) or lobeline (0.01–100 $\mu$M) was added to the superfusion buffer of individual chambers after the collection of the second basal sample, and the drug remained in the buffer for 60 min or until the end of experiment. Each chamber was exposed to only one concentration of nicotine or lobeline. The concentration-response for each drug was determined using a repeated-measures design. In each experiment, one slice from the same rat was superfused in the absence of drug and served as control. To determine the calcium-dependency of the effect of lobeline, concentration-response experiments were performed as described above, however, slices were superfused in the absence of $CaCl_2$, and 0.5 mM EGTA was added to the superfusion buffer.

To determine the ability of mecamylamine to antagonize nicotine-evoked [$^3$H]overflow, a repeated-measure design was utilized also. Individual slices were superfused with a single concentration (0.01–100 $\mu$M) of mecamylamine for 60 min, followed by 60 min of superfusion with nicotine (10 $\mu$M) in the presence of the various mecamylamine concentrations. One slice in each experiment was superfused in the absence of mecamylamine to determine the effect of nicotine alone. A control slice was superfused with buffer alone. To determine the ability of mecamylamine to antagonize lobeline-evoked [$^3$H]overflow, a between-groups design was utilized. Slices were superfused for 60 min in the absence or presence of different concentrations (1–100 $\mu$M) of mecamylamine, a between-group factor, followed by super-fusion for 60 min with a range of concentrations (0.1–100 $\mu$M) of lobeline, a within-group factor.

At the end of each experiment, each slice was solubilized with TS-2, and was incubated at room temperature overnight. The pH and volume of the solubilized tissue samples were adjusted to those of the superfusate samples. Radioactivity in the superfusate and tissue samples was determined by liquid scintillation counting (Packard model B1600 TR Scintillation Counter) with an efficiency of 59%.

Fractional release for each superfusate sample was calculated by dividing the tritium collected in each sample by the total tritium present in the tissue at the time of sample collection. Fractional release was expressed as a percentage of total tritium in the tissue at the time of sample collection. Basal outflow was calculated from the average of the tritium collected in the two 5-min samples just before the addition of drug. Nicotine or lobeline-evoked [$^3$H]overflow was calculated by summing the increases in collected tritium resulting from exposure to drug and subtracting the basal outflow for the equivalent period of drug exposure.

Example 3
Determination of Endogenous DA and DOPAC Content in Striatal Slices Following Superfusion with Lobeline To determine if lobeline exposure depleted endogenous DA content in the striatal slices, superfusion experiments were performed exactly as described above, except that slices were preloaded with 0.1 $\mu$M unlabeled DA, rather than the same concentration of [$^3$H]DA. At the end of the superfusion experiment, slices were processed in the endogenous DA and DOPAC content assay described below.

Example 4
Striatal DA and DOPAC Content Assay

Striatal slices from superfusion experiments and striatal tissue from rats administered lobeline or vehicle in in vivo studies were assayed for endogenous DA and DOPAC content by a modification of a previously described method (Dubocovich and Zahniser, 1985). An aliquot (500$\mu$l) of 0.1M perchloric acid (pH 1.0) containing 0.14–0.29 $\mu$M 3,4-dihydroxybenzylamine hydrobromide (DHBA, internal standard) was added to 100 mg of striatum and the mixture was sonicated with an Ultrasonic Processor (40-Watt Model, Sonics & Materials, Danbury, Conn.). The homogenate was centrifuged at 30,000×g for 10 min at 4° C., and the supernatant was filtered (0.2 $\mu$m nylon membrane). An aliquot (50 $\mu$l) of the filtrate (1:1, 1:50, 1:100, 1:200 or 1:500 dilution with 0.1M perchloric acid) was injected onto the high pressure liquid chromatograph with electrochemical detection (HPLC-EC) system. The HPLC-EC system consisted of syringe loading injector (Model 7725, Rheodyne L.P., Cotati, Calif.), Beckman Model 116 HPLC pump (Beckman, Fullerton, Calif.), ESA ODS ultrasphere C18 reverse-phase column (4.6 cm×75 mm, 3 micron particle size, ESA, Bedford, Mass.), and an ESA 5100A coulometric electrochemical detector with a model 5011 detector cell (E1=+0.05 V, E2 =+0.32 V). The eluent was 6% acetonitrile, 10 $\mu$M EDTA, 1.4 mM 1-octane-sulfonic acid and 76 mM sodium phosphate monobasic (pH 3.1). All separations were performed at room temperature at a flow rate of 1 ml/min. Complete separation of DA and DOPAC and re-equilibration of the system required 9 min. The retention time of DA, DOPAC and DHBA standards was used to identify the relevant peak. Peak heights were used to calculate the detected amount of compound based on standard curves. The detection limit of DA and DOPAC was 0.2 and 0.05 pg/50 $\mu$l injected, respectively. Recovery of internal standard was routinely 75%.

Example 5
[$^3$H]DA Uptake Assay, Striatal Synaptosomal Preparation

The uptake of [$^3$H]DA into striatal synaptosomes was determined using a modification of a previously published method (Masserano et al., 1994). The striata from a single rat were homogenized in 20 ml cold 0.32M sucrose with 5 mM $NaHCO_3$ (pH 7.4) with 16 up and down strokes of a TEFLON pestle homogenizer (clearance approximately 0.003 inches). The homogenate was centrifuged at 2,000×g for 10 min at 4° C. The supernatant was centrifuged at 20,000×g for 15 min at 4° C. The pellet was resuspended in 2 ml assay buffer (in mM; 125 NaCl, 5KCl, 1.5 $MgSO_4$, 1.25 $CaCl_2$, 1.5 $KH_2PO_4$, 10 $\alpha$-D-glucose, 25 HEPES, 0.1 EDTA, 0.1 pargyline, 0.1 ascorbic acid, and saturated with 95% $O_2$/5% $CO_2$, pH 7.4). The final protein concentration was 400 $\mu$g/ml. The assay was performed in duplicate in a total volume of 500 $\mu$l. Aliquots (50 $\mu$l containing 20 $\mu$g of protein) were incubated with 50 $\mu$l of nicotine (final concentration 0.001 nM–100 $\mu$M) or 50 $\mu$l of lobeline (final concentration, 0.01–1000 $\mu$M) in a metabolic shaker at 34° C. for 10 min. Subsequently, a final DA ([$^3$H]DA/cold DA) concentration of 0.32 $\mu$M was added to each tube in a total volume of 66 $\mu$l, consisting of 16 $\mu$l of 0.01 $\mu$M [$^3$H]DA and 50 $\mu$l of 3 $\mu$M unlabelled DA. The incubation continued for 10 min at 34° C. The reaction was terminated by the addition of 3 ml cold assay buffer (without 1 mM catechol). Samples were rapidly filtered through a Whatman GF/B filter using a Brandel cell harvester (model MP-43RS, Biochemical Research and Development Laboratories, Inc., Gaithersburg, Md.) and the filter was subsequently washed 3 times with 4 ml of cold assay buffer containing 1 mM catechol. Filters were previously soaked for 2 hrs in the cold assay buffer containing 1 mM catechol. Nonspecific uptake was determined in duplicate samples in the presence of 10 μM GBR 12909. Filters were placed into scintillation vials, 10 ml of scintillation cocktail was added and radioactivity was determined by scintillation spectrometry.

Example 6

[$^3$H]DA Uptake, Striatal Synaptic Vesicle Preparation

The uptake of [$^3$H]DA into striatal synaptic vesicles was determined using previously published methods (Erickson et al., 1990). Striata from 3 rats were pooled and homogenized in 0.32M sucrose (pH 7.5, 500 mg/14 ml) with 10 up and down strokes of a TEFLON pestle (clearance approximately 0.009 inches) over a 2 min period. The homogenate was then centrifuged at 2,000×g for 10 min at 4° C. and the resulting supernatant was centrifuged at 10,000×g for 30 min at 4° C. Synaptosomes (buffy coat) were separated from the underlying mitochondria and cellular debris (reddish pellet) by gentle swirling in 2 ml of 0.32M sucrose. The enriched synaptosome fraction (2.0 ml) was subjected to osmotic shock by addition of 7 ml distilled $H_2O$ and was homogenized with 5 up and down strokes of the TEFLON pestle. The osmolarity was restored by the addition of 900 μl of 0.25M HEPES and 900 μl of 1.0M neutral potassium-tatrate buffer (pH 7.5) followed by a 20 min centrifugation (20, 000×g at 4° C.). The supernatant was then centrifuged for 60 min (55,000×g at 4° C.). One ml of solution containing 10 mM $MgSO_4$, 0.25M HEPES and 1.0M potassium-tartrate buffer was added to the supernatant and the suspension was centrifuged (100,000×g for 45 min at 4° C.). Immediately before use, the final pellet was resuspended in the assay buffer (in mM; 25 HEPES, 100 potassium tartrate, 0.05 EGTA, 0.10 EDTA, 2 ATP-$Mg^{2+}$, 1.7 ascorbic acid, pH 7.4). Aliquots (160 μl containing 8–10 μg protein) of the resuspension were incubated with 20 μl of drug (nicotine, final concentration 0.001–1000 μM; lobeline, final concentration 0.001–100 μM; or tetrabenazine, final concentration 0.001–100 μM) and 20 μl of [$^3$H]DA (final concentration 0.3 μM) for 8 min at 37° C. in a total volume of 200 μl. The reaction was terminated by addition 2.5 ml of cold assay buffer containing 2 mM $MgSO_4$. Samples were rapidly filtered through Whatman GF/F filters using the Brandel cell harvester. The filters were then washed 3 times with 4 ml of cold assay buffer containing 2mM $MgSO_4$. Filters were previously soaked in 0.5% polyethylenimine (PEI) solution for 2 hr at 4° C. Nonspecific uptake was determined by incubation of duplicate samples at 0° C. in the absence of drug. Filters were placed into scintillation vials, 10 ml of scintillation cocktail was added to each vial, and radioactivity was determined by scintillation spectrometry.

Example 7

Electron Microscopy

To confirm the purity of the isolated synaptic vesicles, vesicle pellets from rat striata were processed for electron microscopy. The pellet was fixed for 2 hr with 3.5% glutaraldehyde in 0.1M phosphate buffer (pH 7.3). After a brief rinse in phosphate buffer, the pellet was postfixed for 2 hr in 1% osmium tetroxide in phosphate buffer. The pellet was then dehydrated five times in graded ethanol (50%, 70%, 80%, 90% and 100%), and embedded in Eponate 12 resin. Ultrathin (60–80 nm) sections were cut on an Ultracut E microtome (Reichert-Jung, Inc., Vienna, Austria) and were collected on copper grids. The sections were then stained with saturated uranyl acetate in 70% ethanol and 0.04M lead citrate. The grids were viewed with a Hitachi H-7000 transmission electron microscope (Hitachi, Tokyo, Japan).

Example 8

Statistics

Repeated-measures, one-way ANOVA was performed to analyze the results of the following experiments: the concentration effect of nicotine or lobeline on [$^3$H]overflow, the ability of mecamylamine to antagonize nicotine (10 μM)-evoked [$^3$H]overflow, and the effect of lobeline on DA and DOPAC content in striatal slices. Two-way ANOVAs were used to analyze the concentration effect of lobeline or nicotine on the time course of fractional release, to analyze the calcium-dependency of lobeline-evoked [$^3$H]overflow and to analyze mecamylamine antagonism of lobeline-evoked [$^3$H]overflow. Inhibition of synaptosomal and vesicular [$^3$H]DA uptake were analyzed by repeated-measures, one-way ANOVA, and by an iterative nonlinear least-squares curve-fitting program (GraphPAD-PRIZM; GraphPAD, San Diego, Calif.) to obtain $IC_{50}$ values. Dunnett's post hoc test was used to compare treatment means to a single control mean. Also, Duncan's New Multiple Range Test or Fisher's LSD post hoc analysis were used to compare pairs of treatment means. Duncan's New Multiple Range Test was used when significant one-way ANOVA's were obtained or when significant main effects were obtained in the two-way ANOVA's. Fisher's LSD poste hoc analysis is a more conservative test, which takes into account error which cumulates during multiple comparisons of pairs of means. Fisher's LSD analysis was used when the interaction term was significant in the two-way ANOVAs, specifically in the post hoc analysis of drug×time interactions. Statistical significance was reached when P<0.05 (two-tailed, unless otherwise indicated).

Conclusion

The results of the present study demonstrate that, similar to nicotine, lobeline evokes [$^3$H]overflow from rat striatal slices preloaded with [$^3$H]DA in a concentration-dependent manner. However, in contrast to nicotine, lobeline-evoked [$^3$H]overflow is calcium-independent and mecamylamine-insensitive. Although lobeline is often thought to be a nicotinic agonist, the present results suggest that lobeline acts to evoke [$^3$H]overflow via a mechanism other than by stimulation of nicotinic receptors. Moreover, in contrast to nicotine, lobeline potently inhibits striatal synaptosomal and vesicular [$^3$H]DA uptake. Thus, lobeline-induced inhibition of DA uptake and alteration of intracellular DA storage may contribute to the mechanism responsible for the lobeline-evoked increase in [$^3$H]overflow from [$^3$H]DA -preloaded striatal slices.

In agreement with reports of others, nicotine evoked [$^3$H]overflow from superfused rat striatal slices preloaded with [$^3$H]DA (Westfall, 1974; Giorguieff-Chesselet et al., 1979; Westfall et al., 1987; Harsing et al., 1992; Sacaan et al., 1995) and from rat or mouse striatal synaptosomes (Chesselet, 1984; Rowell et al, 1987; Rapier et al., 1988, 1990; Grady et al., 1992; Rowell and Hilelbrand, 1992, 1994; Rowell, 1995). The nicotine concentration range (0.001–100 μM) chosen for the present study was based on extensive research demonstrating that at low concentrations (<100 μM), the effect of nicotine was calcium-dependent and antagonized by mecamylamine (i.e., nicotinic receptor-mediated); whereas at high concentrations (>100 μM), a calcium-independent effect which was not antagonized by mecamylamine was observed (Giorguieff-Chesselet et al., 1979; Westfall et al., 1987; Rapier et al., 1988, 1990; Grady et al., 1992).

In previous studies utilizing the slice superfusion assay, nicotine was superfused for only short periods of time (3–10 min) (Giorguieff-Chesselet et al., 1979; Westfall et al., 1987; Harsing et al., 1992; Sacaan et al., 1995). Only one of these reports (Giorguieff-Chesselet et al., 1979) provided the time course of the effect of nicotine (1 μM), and in that study, [$^3$H]overflow remained elevated for the entire 10-min period of nicotine exposure. The present study illustrates a complete time course of exposure (over a 60 min superfusion period) to a low range of nicotine concentrations (0.01–100 μM) (FIG. 1A), and illustrates the time course and pattern of mecamylamine-induced inhibition of the effect of nicotine, indicative of nicotinic receptor mediation (FIG. 4). The time course illustrates that the peak effect of nicotine was reached within 10–15 min after the start of superfusion with drug. Despite continued superfusion with nicotine, the response returned to basal levels within 25 min, indicative of receptor desensitization. The present findings are of particular interest considering that in human smokers, a persistent nicotine blood level (0.1–μM) has been observed during the waking hours of each day (Benowitz et al., 1990).

Similar to nicotine, lobeline evoked [$^3$H]overflow from [$^3$H]DA-preloaded striatal slices in a concentration-dependent manner. However, as illustrated by the time course (FIG. 2) and the concentration-response curve (FIG. 3), the pattern and the magnitude of the effect of lobeline was different from that of nicotine. The peak effect occurred 10–20 min following the start of lobeline exposure and, at least at the low concentrations, the response returned to basal levels despite continued superfusion with lobeline. However, the response remained significantly above basal levels during superfusion with the higher lobeline concentrations (30–100 μM). Moreover, the effect of lobeline on [$^3$H]overflow was markedly increased (8–34 fold) compared to the effect of nicotine, particularly at the higher concentrations (10–100 μM) examined (FIGS. 1B and 3). Additionally, a depletion of endogenous DA and an increase in endogenous DOPAC was observed in the striatal slices superfused with these high concentrations of lobe-line, indicative of marked DA utilization in response to lobeline, and potential toxicity, at least in vitro (FIG. 6). Furthermore, in contrast to nicotine, the effect of lobeline was found in the present study to be calcium-independent and not inhibited by mecamylamine. Thus, despite the reported high affinity of lobeline for the [$^3$H]nicotine binding site, lobeline evidently evokes [$^3$H]overflow from rat striatal slices preloaded with [$^3$H]DA by a mechanism other than stimulation of nicotinic receptors.

The present results further demonstrate that, in contrast to nicotine, lobeline potently inhibits [$^3$H]DA uptake into striatal synaptosomes and vesicles. Significant inhibition of [$^3$H]DA uptake into synaptic vesicles was observed at a low concentration of 0.3 μM of lobeline, and the $IC_{50}$ for this effect was 0.88 μM (FIG. 5). Additionally, at higher concentrations ($\geq$30 μM), [$^3$H]DA uptake into striatal synaptosomes was also significantly inhibited. The $IC_{50}$ for lobeline-induced inhibition of synaptosomal uptake was 80 μM, i.e., two orders of magnitude higher than that for inhibition of uptake into synaptic vesicles. The present results from the synaptosomal assay are in good agreement with a previous report of lobeline-induced inhibition of [$^3$H]DA uptake into mouse striatal synaptosomes (Debler et al., 1988). In the present study, nicotine only inhibited vesicular [$^3$H]DA uptake at a very high concentration (~1 mM) and no inhibition of synaptosomal [$^3$H]DA uptake was observed. The lack of effect of nicotine to inhibit DA uptake into striatal synaptosomes is in agreement with previous reports (Kramer et al, 1989; Izenwasser et al., 1991; Rowell and Hill, 1993). Using the striatal mince preparation, nicotine has been reported to inhibit [$^3$H]DA uptake by an indirect mechanism (Izenwasser et al., 1991); however, other investigators using the more intact striatal slice preparation were unable to observe any nicotine-induced inhibition of [$^3$H]DA uptake (Rowell and Hill, 1993). Interestingly, [$^3$H]DA uptake into β-NGF-treated PC12 cells transfected with the rat DA transporter cDNA was inhibited by nicotine ($IC_{50}$=8 μM), and mecamylamine blocked nicotine's effects (Yamashita et al, 1995), suggesting that nicotinic receptors may modulate DA uptake. More recently, nicotine (0.4 mg/kg) administered s.c. to rats was observed to increase the clearance of exogenously applied DA in an in vivo voltammetric study (Hart and Ksir, 1996), suggesting nicotine-induced enhancement of DA clearance in striatum in vivo. The results of the present study indicate that the synaptic vesicular DA transporter is significantly more sensitive to lobeline-induced inhibition than the plasma membrane DA transporter, and that both transport processes are not modulated to any great extent by nicotine. Since these two transporters are structurally and functionally different (see review, Brownstein and Hoffman, 1994), it is not surprising that they are differentially sensitive to inhibition by lobeline.

The lobeline-induced increase in DA concentration in the extracellular space (as reflected by an increase in [$^3$H] overflow in superfusate in the [$^3$H]DA release assay) is consistent with the lobeline-induced inhibition of vesicular and synaptosomal DA uptake. Notably, the lowest concentration of lobeline to significantly evoke [$^3$H]overflow in the superfusion assay was 1 μM, which is within the range of concentrations observed to specifically inhibit vesicular DA uptake, since higher concentrations (i.e. >30 μM) were required to detect the inhibition of synaptosomal DA uptake. The observation that the lobeline-induced [$^3$H]overflow is not calcium-dependent suggests that the released DA originated from cytosolic rather than vesicular pools. Since lobeline is a very lipophilic compound (Barlow and Johnson, 1989; Reavill et al, 1990; Bhat et al., 1991), it could easily gain access to the vesicular transporter by passive entrance into the neuron and its vesicles. Lobeline-induced inhibition of vesicular DA uptake could occur via two mechanisms, dissipation of the vesicle proton gradients and/or interaction with a substrate site on the vesicular transporter. Because lobeline is a weak base, and as a result of the lower pH inside the vesicle, lobeline could accumulate in synaptic vesicles in its charged form (i.e. protonated). Once lobeline exceeded the buffering capacity within the vesicle, the vesicular pH gradient would be attenuated with a resulting decrease in available energy for DA uptake (Beers et al., 1986; Johnson, 1988). Subsequently, uncharged DA would diffuse out of the vesicles in accordance with the concentration gradient, such that DA concentrations in the cytosol would increase. Elevation of cytosolic DA would promote reverse transport and DA release from the presynaptic terminal into the extracellular space. Furthermore, neurotoxicity may result from the increased cytosolic DA, which could likely undergo auto-oxidation and enzymatic oxidative metabolism, leading to the increased formation of DOPAC, hydrogen peroxide, free radicals, and active quinones (Graham et al., 1978; Slivka and Cohen, 1985). Thus, lobeline-induced redistribution of intracellular DA within the presynaptic terminal would result in DA release and potential neurotoxicity.

Taken together, lobeline appears to act in an amphetamine-like manner as a DA releasing agent. Amphetamine is lipophilic, entering neurons by passive diffusion (Ross and Renyi, 1966; Fischer and Cho, 1989; Liang and Rutledge, 1982). At low concentrations, amphetamine enters neurons via the DA transporter; and as a result, DA is released into the extracellular space by carrier-mediated exchange diffusion (Fischer and Cho, 1979; Liang and Rutldege, 1982), a calcium-independent mechanism which is sensitive to DA uptake inhibitors (Hurd and Ungerstedt, 1989; Parker and Cubeddu, 1986; Zaczek et al., 1991; Levi and Raiteri, 1993). Furthermore, amphetamine is a weak base which has been reported to interact with the vesicular substrate site (Schuldiner et al, 1993; Gonzalez et al., 1994), to enter synaptic vesicles, and dissipate the vesicular proton gradient resulting in intracellular redistribution and subsequent release of neurotransmitter (Knepper et al., 1988; Sulzer and Rayport, 1990; Sulzer et al., 1995). In comparison with amphetamine, few studies have focused on the mechanism of action of lobeline; however, the present findings indicate many similarities in the action of these two drugs, even though lobeline has often been categorized as a nicotinic agonist (Decker et al, 1995).

The current observation, that superfusion of striatal slices with high concentrations (30–100 $\mu$M) of lobeline resulted in significant DA depletion, led us to evaluate striatal DA content following acute, intermittent and chronic in vivo lobeline administration to rats. Only one study has reported a brain concentration (0.6 $\mu$M) of lobeline 15 min following in vivo administration (4 mg/kg, s.c.) to rats (Reavill et al., 1990). Thus, in the present study, in order to obtain higher brain concentrations, lobeline was administered to rats in doses up to 30 mg/kg for 21 days. No effect on endogenous DA or DOPAC content was observed following any dose or treatment regimen of lobeline administration. The present results are in agreement with a previous study in which lobeline was administered acutely at a single dose (10 mg/kg, i.p.) and no effect on DA striatal content was observed (Westfall et al., 1967). The highly lipophilic nature of lobeline and its ability to cross the blood-brain barrier results in a higher brain/plasma ratio compared to nicotine following s.c. administration (Barlow and Johnson, 1989; Reavill et al., 1990; Bhat et al., 1991). Due to the physicochemical characteristics of lobeline, high concentrations in brain after in vivo administration (as are required in the superfusion buffer to observe the striatal DA depletion) may not be achieved due to metabolic/pharmacokinetic factors. Furthermore, chronic administration of lobeline via osmotic minipump may not have delivered the expected dose, due to potential instability of the drug at 37° C. for prolonged time periods (Dr. Yvonne Boyer, DynaGen, Inc., personal communication). However, striatal DA depletion was not observed following 10 days of intermittent administration of 10 mg/kg, prepared fresh each day without the possibility of lobeline instability. Nevertheless, the use of lobeline as a long-term smoking cessation therapy should be carefully evaluated with respect to potential CNS neurotoxicity, particularly in light of the apparent similarities of lobeline and amphetamine, and the known neurotoxicity of amphetamine and its analogs (Sonsalla, 1995).

In summary, lobeline evoked [$^3$H]overflow from rat striatal slices preloaded with [$^3$H]DA, in a concentration-dependent, calcium-independent and mecamylamine-insensitive manner. A lobeline-induced inhibition of synaptic vesicular DA transport and subsequent redistribution of presynaptic DA storage may be the mechanism by which lobeline evokes DA release. Clearly, lobeline evokes DA release by a mechanism different from that of nicotine, which may explain the reported differences in the behavioral effects of these drugs, and the differences in their abilities to upregulate nicotinic receptors following chronic administration.

Although the present invention has been discussed hereinabove by way of examples for the purpose of illustration and clarity of understanding, it should be appreciated that the scope of the invention is instead defined by the appended claims and equivalents thereof.

REFERENCES

The pertinent disclosures of the references listed below and as discussed above herein are incoporated herein by reference.

AIZENMAN, E., "Effects of nicotinic agonists on the NMDA receptor," *Brain Res.*, 551:355–357 (1991).

ANDERSON, D. J. et al., "Nicotine receptor binding of [$^3$H]cytisine, [$^3$H]nicotine and [$^3$H]methylcarbamylcholine in rat brain," *Eur. J. Pharmacol.*, 253:261–267 (1994).

BANERJEE, S. et al., "Nicotine antagonists: phosphoinositide turnover and receptor binding to determine muscarinic properties," *Medical Pharmacol.*, 38(17):2933–2935 (1989).

BARLOW, R. B. et al., "Relationship between structure and nicotine-like activity: X-ray crystal structure analysis of (–)cytisine and (–)lobeline hydrochloride and a comparison with (–)nicotine and other nicotine-like compounds," *Br. J. Pharmacol.*, 98:799–808 (1989).

BEERS, M. F. et al., "Evidence for an ascorbate shuttle for the transfer of reducing equivalents across chromaffin granule membranes," *J. Biol. Chem.*, 261:2529–2535 (1986).

BENOWITZ, N. L. et al., "Pharmacokinetics, metabolism, and pharmacodynamics of nicotine," In *Nicotine Psychopharmacology: Molecular, Cellular, and Behavorial Aspects*, ed. by S. Wonnacott, et al., pp.112–157, Oxford University Press, 1990.

BENWELL, M. E. M. et al., "The effects of acute repeated nicotine treatment on nucleus accumbens dopamine and locomotor activity," *Br. J. Pharmacol.*, 105:849–856 (1992).

BENWELL, M. E. M. et al., "Evidence that tobacco smoking increases the density of (–)-[$^3$H]nicotine binding sites in human brain," *J. Neurochem.* 50(4):1243–1247 (1988).

BHAT, R. V. et al., "Regulation of brain nicotinic receptors by chronic agonist infusion," *J. Neurochem.*, 56(6):1932–1939 (1991).

BEHAT, R. V. et al., "Effects of chronic nicotine infusion on kinetics of high-affinity nicotine binding," *J. Neurochem.*, 62:574–581 (1994).

BRAZELL, M. P. et al., "Acute administration of nicotine increases the in vivo extracellular levels of dopamine, 3,4-dihydroxyphenylacetic acid and ascorbic acid preferentially in the nucleus accumbens of the rat: comparison with the caudate-putamen," *Neuropharmacol.*, 29:1177–1185 (1990).

BRIONI, J. D. et al., "Nicotinic receptor agonists exhibit anxiolytic-like effects on the elevated plus-maze test," *Eur. J. Pharmacol.*, 238:1–8 (1993).

BROWNSTEIN, M. J. et al., "Neurotransmitter transporters," *Rec. Prog. Hormone Res.*, 49:27–42 (1994).

BROUSSOLLE, E. P. et al., "In vivo binding of $^3$H-nicotine in the mouse brain," *Life Sci.*, 44:1123–1132 (1989).

CHESSELET, M. F., "Presynaptic regulation of neurotransmitter release in the brain: Facts and hypotheses," *Neurosci.,* 12:347–375 (1984).

CLARKE, P. B. S., "Dopaminergic mechanisms in the locomotor stimulant effects of nicotine," *Biochem. Pharmacol.* 40:1427–1432 (1990).

CLARKE, P. B. S. et al., "The effect of nicotine on locomotor activity in non-tolerant and tolerant rats," *Br. J. Pharmacol.,* 78:329–337 (1983a).

CLARKE, P. B. S. et al., "Characterization of the locomotor stimulant action of nicotine in tolerant rats," *Br. J. Pharmacol.,* 80:587–594 (1983b).

CLARKE, P. B. S. et al., "Apparent absence of nicotine-induced conditioned place preference in rats," *Psychopharmacol.,* 92:84–88 (1987).

CLARKE, P. S. et al., "Autoradiographic evidence for nicotine receptors on nigrostriatal and mesolimbic dopaminergic neurons," *Brain Res.,* 348:355–358 (1985).

COLLINS, A. C. et al., "Dissociation of the apparent relationship between nicotine tolerance and up-regulation of nicotinic receptors," *Brain Res. Bull.,* 25:373–379 (1990).

CORRIGAL, W. A. et al., "The mesolimbic dopaminergic system is implicated in the reinforcing effects of nicotine," *Psychopharmacol.,* 107:285–289 (1992).

CORRIGAL, W. A. et al., "Self-administered nicotine activates the mesolimbic dopamine system through the ventral tegmental area," *Brain Res.,* 653:278–284 (1994).

COURT, J. A. et al., "Nicotine reduces the binding of [$^3$H]MK-801 to brain membranes, but not via the stimulation of high-affinity nicotinic receptors." *Brain Res.,* 524:319–321 (1990).

CUBEDDU, L. X. et al., "Metabolism and efflux of [$^3$H]dopamine in rat neostriatum: Presynaptic origin of 3,4-[$^3$H]dihydroxyphenylacetic acid," *J. Pharmacol. Exp. Ther.,* 209:165–175 (1979).

DAMSMA, G. et al., "Lack of tolerance to nicotine-induced dopamine release in the nucleus accumbens," *Eur. J. Pharmacol.,* 168:363–368 (1989).

DEBLER, E. A. et al., "Ascorbic acid and striatal transport of [$^3$H]1-methyl-4-phenylpyridine (MPP$^+$) and [$^3$H]dopamine," *Life Sci.,* 42:2553–2559 (1988).

DECKER, M. W. et al., "Diversity of neuronal nicotinic acetylcholine receptors: lessons from behavior and implications for CNS therapeutics," *Life Sci.,* 56:545–570 (1995).

DECKER, M. W. et al., "Effects of lobeline, a nicotinic receptor agonist, on learning and memory," *Pharmacol. Biochem. Behav.,* 45:571–576 (1993).

DONNY, E. C. et al.: "Nicotine self-administration in rats," *Psychopharmacol.* (in press).

DORSEY, J. L., "Control of the tobacco habit," *Ann Int. Med.,* 10:628–631 (1936).

DUBOCOVICH, M. L. et al., "Binding characteristics of the dopamine uptake inhibitor [$^3$H]nomifensine to striatal membranes," *Biochem. Pharmacol.,* 34(8):1137–1144 (1985).

DWOSKIN, L. P. et al., "Robust modulation of [$^3$H]dopamine release from rat striatal slices by D-2 dopamine receptors," *J. Pharmacol. Exp. Ther.,* 239:442–453 (1986)

ERICKSON, J. D. et al., "Chloride ion increases [$^3$H]dopamine accumulation by synaptic vesicles purified from rat striatum: inhibition by thiocyanate ion," *Brain Res.,* 516:155–160 (1990).

FISCHER, J. F. et al., "Chemical release of dopamine from striatal homogenates: evidence for an exchange diffusion model," *J. Pharmacol. Exp. Ther.,* 208(2):203–209, (1979).

FUDALA, P. J. et al., "Further studies on nicotine-induced conditioned place preference in the rat," *Pharmacol. Biochem. Behav.,* 25:1041–1049 (1986).

FUDALA, P. J., et al., "Pharmacologic characterization of nicotine-induced conditioned place preference," *Pharmacol. Biochem. Behav.,* 22:237–241 (1985).

FUNG, Y. K. et al., "Receptor mechanisms of nicotine-induced locomotor hyperactivity in chronic nicotine treated rats," *Eur. J. Pharmacol.,* 152:263–271 (1988).

GELLER, I. et al., "Effects of nicotine monomethiodide, lobeline, chlordiazepoxide, meprobamate and caffeine on a discrimination task in laboratory rats," *Psychopharmacol. (Berl.),* 20:355–365 (1971).

GIORGUIEFF-CHESSELET, M. F. et al., "Regulation of dopamine release by presynaptic nicotinic receptors in rat striatal slices: effect of nicotine in a low concentration," *Life Sci.,* 25:1257–1262 (1979).

GONZALEZ, A. M. et al., "Synaptic vesicular monoamine transporter expression: distribution and pharmacologic profile," *Mol. Brain Res.,* 22:219–226 (1994).

GRADY, S. et al., "Characterization of nicotine receptor-mediated $^3$H-dopamine release from synaptosomes prepared from mouse striatum," *J. Neurochem.,* 59:848–856 (1992).

GRADY, S. R., et al., "Desensitization of nicotine-stimulated [$^3$H]dopamine release from mouse striatal synaptosomes," *J. Neurochem.,* 62:1390–1398 (1994).

GRAHAM, D. G., et al., "Autoxidation versus covalent binding of quinones as the mechanism of toxicity of dopamine, 6-hydroxydopamine, and related compounds towards C1300 neuroblastoma cells in vitro," *Mol. Pharmacol.,* 14:644–653 (1978).

HAMANN, S. R. et al., "Hyperalgesic and analgesic actions of morphine, U50-488, naltrexone, and (−)lobeline in the rat brainstem," *Pharmacol. Biochem. Behav.,* 47:197–201 (1994).

HARSING, L. G. et al., "Dopamine efflux from striatum after chronic nicotine: evidence for autoreceptor desensitization," *J. Neurochem.,* 59:48–54 (1992).

HART, C. et al., "Nicotine effects on dopamine clearance in rat nucleus accumbens," *J. Neurochem.,* 66(1):216–221, (1996).

HURD, Y. L. et al., "Ca$^{2+}$dependence of the amphetamine, nomifensine, and Lu 19-005 effect on in vivo dopamine transmission," *Eur. J. Pharmacol.,* 166:261–269 (1989).

IMPERATO, A. et al., "Nicotine preferentially stimulates dopamine release in the limbic system of freely moving rats," *Eur. J. Pharm.,* 132:337–338 (1986).

IZENWASSER, S. et al., "Nicotine indirectly inhibits [$^3$H]dopamine uptake at concentrations that do not directly promote [$^3$H]dopamine release in rat striatum," *J. Neurochem.,* 56(2):603–610 (1991).

JOHNSON, R. G., "Accumulation of biological amines into chromaffin granules: a model for hormone and neurotransmitter transport," *Physiol. Rev.,* 68:232–307 (1988).

JOHNSON, K. M. et al., "Pharmacological evidence for N-methyl-D-aspartate receptors on nigrostriatal dopaminergic nerve terminals," *Can. J. Physiol. Pharmacol.,* 69:1416–1421 (1991).

KALYUZHNYY, V. V., "The treatment of nicotinism with the aid of lobeline and its influence on vegetative and vascular reactions," *J. Neural. Psychiat.,* 68:1864–1870 (1968).

KNEPPER, S. M. et al., "Inhibition of norepinephrine transport into synaptic vesicles by amphetamine analogs," *J. Pharmaco. Exp. Ther.,* 247(2):487–494 (1988).

KRAMER, H. K. et al., "The effect of nicotine on catecholaminergic storage vesicles," *Brain Res.*, 503:296–298 (1989).

LEVI, G. et al., "Carrier-mediated release of neurotransmitters," *TINS.*, 16(10):415–419 (1993).

LIANG, N. Y. et al.: "Comparison of the release of [$^3$H]dopamine from isolated corpus striatum by amphetamine, fenfluramine and unlabelled dopamine," *Biochem. Physiol.*, 31:983–992 (1982).

LIPPIELLO, P. M. et al., "The binding of L-[$^3$H]nicotine to a single class of high affinity sites in rat brain membrane," *Mol. Pharmacol.*, 29:448–454 (1986).

LOIACONO, R. et al., "Multiple binding sites for nicotine receptor antagonists in inhibiting [$^3$H](−)-nicotine binding in rat cortex," *Neuropharmacol.*, 32:847–853 (1993).

MARKS, M. J. et al., "Nicotine binding and nicotinic receptor subunit RNA after chronic nicotine treatment," *J. Neurosci.*, 12(7):2765–2784 (1992). MASSERANO, J. M. et al., "Effects of chronic cocaine administration on [$^3$H] dopamine uptake in the nucleus accumbens, striatum and frontal cortex of rats," *J. Pharmacol. Exp. Ther.*, 270(1):133–141 (1994).

NUNN-THOMPSON et al., "Pharmacotherapy for smoking cessation," *Clin. Pharmacy.*, 8:710–720 (1989).

OLIN, B. R. et al., "Smoking Deterrents," In *Drug Facts and Comparisons*. 1995 edition, ed. by B. R. Olin et al., pp. 3087–3095, St. Louis, Mo.: J. B. Lippincott Co., 1995.

PARKER, E. M. et al., "Effects of d-amphetamine and dopamine synthesis inhibitors on dopamine and acetylcholine neurotransmission in the striatum. I. Release in the absence of vesicular transmitter stores," *J. Pharmacol. Exp. Ther.*, 237(1):179–192 (1986).

PENG, O. et al., "Nicotine-induced increase in the neuronal nicotinic receptors results from a decrease in the rate of receptor turnover," *Mol. Pharmacol.*, 46:523–530 (1994).

PRIGNOT, J., "Pharmacological approach to smoking cessation," *Eur. Respir. J.*, 2:550–560 (1989).

RAPIER, C. et al., "Stereoselective nicotine-induced release of dopamine from striatal synaptosomes: concentration dependent and repetitive stimulation," *J. Neurochem.*, 50(4):1123–1130 (1988).

RAPIER, C. et al., "Nicotine modulation of [$^3$H] dopamine release from striatal synaptosomes: pharmacological characterization," *J. Neurochem.*, 50:1123–1130 (1990).

REAVILL, C. et al.: "High affinity binding of [$^3$H](−)-nicotine to rat brain membranes and its inhibition by analogues of nicotine," *Neuropharmacol.*, 27(3):235–241 (1988).

REAVILL, C. et al., "Behavioral and pharmacokinetics studies on nicotine, cytosine and lobeline," *Neuropharmacol.*, 29(7):619–624 (1990).

REYNOLDS, I. J. et al., "[$^3$H]MK801 binding to the N-methyl-D-aspartate receptor reveals drug interactions with zinc and magnesium binding sites," *J. Pharmacol. Exp. Ther.*, 247(3):1025–1031 (1988).

ROMANO, C. et al., "Sterespecific nicotine receptors on rat brain membranes," *Science*, 210:647–650 (1980).

ROMM, E. et al., "Purification of L-[$^3$H]nicotine eliminates low affinity binding," *Life Sci.*, 46:935–946 (1990).

ROSS, B. et al., "Uptake of some tritiated sympathomimetic amines by mouse brain cortex slices in vitro," *Acta Pharmacologica*, 24:297–309 (1966).

ROWELL, P. P.: "Nanomolar concentrations of nicotine increase the release of [$^3$H]dopamine from rat striatal synaptosomes," *Neurosci. Lett.*, 189:171–175 (1995).

ROWELL, P. P. et al., "Apparent inability of nicotine to inhibit dopamine uptake into rat striatal tissue in vitro," *The Pharmacologist.*, 35:134 (1993).

ROWELL, P. P. et al., "Desensitization of nicotine-stimulated dopamine release from rat striatal synaptosomes," *The Pharmacologist*, 34:154 (1992).

ROWELL, P. P. et al., "Characterization of nicotine-induced desensitization of evoked dopamine release from rat striatal synaptosomes," *J. Neurochem.*, 63:561–569 (1994).

ROWELL, P. P. et al., "Stimulation of [$^3$H]dopamine release by nicotine in rat nucleus accumbens," *J. Neurochem.*, 49:1149–1154 (1987).

SAKURAI, Y. et al., "Enhancement of [$^3$H]dopamine release and its [$^3$H]metabolites in rat striatum by nicotinic drugs," *Brain Res.*, 242:99–106 (1982).

SANDERSON, E. M. et al., "Upregulation of nicotinic receptors following continuous infusion of nicotine is brain-region-specific," *Brain Res.*, 617:349–352 (1993).

SACAAN, A. I. et al., "Pharmacological characterization of neuronal acetylcholine gated ion channel receptor-mediated hippocampal norepinephrine and striatal dopamine release from rat brain slices," *J. Pharmacol. Exp. Ther.*, 274(1):224–230 (1995).

SCHECHTER, M. D. et al., "Nicotine as a discriminative cue in rats: inability of related drugs to produce a nicotine-like cuing effect," *Psychopharmacol. (Berl.)*, 27:379–387 (1972).

SCHULDINER, S. et al., "Amphetamine derivatives interact with both plasma membrane and secretory vesicle biogenic amine transporter," *Mol. Pharmacol.*, 44:1227–1231 (1993).

SHOAIB, M. et al., "Nicotine-induced place preferences following prior nicotine exposure in rat," *Psychopharmacol.*, 113:445–452 (1984).

SLIVKA, A. et al., "Hydroxyl radical attack on dopamine," *J. Biol. Chem.*, 260:15446–15472 (1985).

SLOAN, J. W. et al., "The competitive binding characteristics of nicotinic ligands and their pharmacology," *Pharmacol. Biochem. Behav.*, 30:255–267 (1988).

SONSALLA, P. K., "The role of N-methyl-D-aspartate receptors in dopaminergic neuropathology produced by the amphetamines," *Drug Alcohol Depend.*, 37:101–105 (1995).

STOLERMAN, I. P. et al., "Dissociation between the locomotor stimulant and depressant effects of nicotinic agonists in rats," *Psychopharmacol.*, 117:430–437 (1995).

SULZER, D. et al., "Amphetamine and other psychostimulants reduce pH gradient in midbrain dopaminergic neurons and chromaffin granules: A mechanism of action," *Neurons*, 5:797–808 (1990).

SULZER, D. et al., "Amphetamine redistributes dopamine from synaptic vesicles to the cytosol and promotes reverse transport," *J. Neurosci.*, 15(5):4102–4108 (1995).

TAKANO, Y. et al., "Presynaptic modulation of the release of dopamine from striatal synaptosomes: difference in the effects of high K$^+$stimulation, methamphetamine and nicotinic drugs," *Brain Res.*, 279:330–334 (1983).

TOTH, E. et al., "Effect of nicotine on extracellular levels of neurotransmitters assessed by microdialysis in various brain regions: Role of glutamic acid," *Neurochem. Res.*, 17:265–271 (1992).

VARANDA, W. A. et al., "The acetylcholine receptor of the neuromuscular junction recognizes mecamylamine as a noncompetitive antagonist," *Mol. Pharmacol.* 28:128–137 (1985).

WESTFALL, T. C. et al., "Effect of nicotine and other drugs on the release of [³H]norepinephrine and [¹⁴C] dopamine in rat brain striatum and hypothalamus slices," *Neuropharmacol.*, 13:1025–1032 (1974).

WESTFALL, T. C. et al., "Effect of nicotine and related substances upon amine levels in the brain," *Ann. N.Y. Acad. Sci.*, 142:83–100 (1967).

WESTFALL, T. C. et al., "Mechanisms of nicotine regulation of dopamine release in neostriatum," In *Tobacco Smoking and Nicotine*, ed. by W. R. Martin et al., pp. 209–223 Plenum, New York, 1987.

WRIGHT, I. S. et al., "Lobeline sulfate: Its pharmacology and use in the treatment of the tobacco habit," *JAMA*, 109:649–654 (1937).

YAMADA, S. et al., "Brain nicotinic acetylcholine receptors biochemical characterization by neosurugatoxin," *Mol. Pharmacol.*, 28:120–127 (1985).

YAMASHITA, H. et al., "Effect of nicotine on dopamine uptake in COS cells possessing the rat dopamine transporter and in PC12 cell," *Biochem. Pharmacol.*, 49(5):742–745 (1995).

ZACZEK, R. et al., "Interactions of [³H]amphetamine with rat brain synaptosomes. II. Active transport," *J. Pharmacol. Exp. Ther.*, 257:830–835 (1991).

ZUMSTEIN, A. K. et al.: "Pathways of dopamine metabolism in rabbit caudate nucleus in vitro," *Naunyn-Schmiedeberg's Arch. Pharmacol.*, 316:205–217 (1981).

What is claimed is:

1. A method of treating an individual for dependence on a drug of abuse, withdrawal from a drug of abuse, or for an eating disorder, wherein said drug of abuse is selected from the group consisting of cocaine, amphetamines, caffeine, phencyclidine, opiates, barbiturates, benzodiazepines, cannabinoids, hallucinogens and alcohol, comprising administering to the individual an effective amount of a compound having the formula wherein $R^1$ and $R^2$ are independently H, lower alkyl, lower alkenyl, lower alkylcarbonyl, phenylcarbonyl, alkylphenylcarbonyl, lower alkoxycarbonyl, lower alkylaminocarbonyl, higher alkylcarbonyl, and poly (alkyleneoxide)carbonyl; $R^3$ is H or combines with $R^1$ to form a double bond; $R^4$ is H or combines with $R^2$ to form a double bond; and X is H or lower alkyl, or pharmaceutically acceptable salt thereof.

2. The method of claim 1, wherein the compound is selected from the group consisting of lobeline, lobelanidine, lobelanine, and pharmaceutically acceptable salts thereof.

3. The method of claim 1, wherein the compound is lobeline, and pharmaceutically acceptable salts thereof.

4. The method of claim 1, wherein said administering is performed subcutaneously, intramuscularly, intravenously, transdermally, orally, intranasally, or rectally.

5. The method of claim 1, wherein said administering of lobeline induces release of dopamine from cells of the central nervous system of the individual.

6. The method of claim 1, wherein said administering of lobeline inhibits uptake of dopamine by cells of the central nervous system of the individual.

7. The method of claim 1, wherein the eating disorder includes obesity of the individual.

8. The method of claim 1, wherein the individual's desire for said drug of abuse or for food is reduced for at least one day.

9. The method of claim 1, further comprising administering behavior modification counseling to the individual.

* * * * *